United States Patent
Van Kranenburg et al.

(10) Patent No.: US 10,273,509 B2
(45) Date of Patent: Apr. 30, 2019

(54) GENETIC MODIFICATION OF (S)-LACTIC ACID PRODUCING THERMOPHILIC BACTERIA

(71) Applicant: PURAC BIOCHEM B.V., Gorinchem (NL)

(72) Inventors: Richard Van Kranenburg, Gorinchem (NL); Anna Verhoef, Gorinchem (NL); Marinus Petrus Machielsen, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 15/327,621

(22) PCT Filed: Jul. 13, 2015

(86) PCT No.: PCT/EP2015/065995
§ 371 (c)(1),
(2) Date: Jan. 19, 2017

(87) PCT Pub. No.: WO2016/012298
PCT Pub. Date: Jan. 28, 2016

(65) Prior Publication Data
US 2017/0298398 A1     Oct. 19, 2017

(30) Foreign Application Priority Data
Jul. 23, 2014   (EP) .................................... 14178150

(51) Int. Cl.
| | | |
|---|---|---|
| C12P 7/56 | (2006.01) | |
| C07K 14/195 | (2006.01) | |
| C12N 9/10 | (2006.01) | |
| C12N 9/88 | (2006.01) | |
| C12N 1/20 | (2006.01) | |

(52) U.S. Cl.
CPC .............. *C12P 7/56* (2013.01); *C07K 14/195* (2013.01); *C12N 1/20* (2013.01); *C12N 9/1029* (2013.01); *C12N 9/88* (2013.01); C12N 2510/00 (2013.01); Y02E 50/17 (2013.01)

(58) Field of Classification Search
None
See application file for complete search history.

(56) References Cited

U.S. PATENT DOCUMENTS

2005/0106694 A1   5/2005   Green et al.

FOREIGN PATENT DOCUMENTS

| EP | 1391502 A1 | 2/2004 |
|---|---|---|
| EP | 1760156 | 3/2007 |
| JP | 2003-47490 A | 2/2003 |
| JP | 2007-49993 A | 3/2007 |
| RU | 2355759 C1 | 5/2009 |
| WO | 01049865 A1 | 7/2001 |
| WO | 03008601 A2 | 1/2003 |
| WO | 2005/086670 A2 | 9/2005 |
| WO | 2006117536 A1 | 11/2006 |
| WO | 2007085433 A1 | 8/2007 |
| WO | 2008038019 A2 | 4/2008 |
| WO | 2010052499 A1 | 5/2010 |
| WO | 2011005554 A2 | 1/2011 |

OTHER PUBLICATIONS

Landmann et al., "Crh, the paralogue of the phosphocarrier protein HPr, controls the methylglyoxal bypass of glycolysis in Bacillus subtilis", Molecular Microbiology (2011) 82(3), 770-787. doi:10.1111/j.1365-2958.2011.07857.x.*

Nazina, T., et al., "Taxonomic study of aerobic thermophilic bacilli," International Journal of Systematic and Evolutionary Microbiology, vol. 51, 2001, pp. 433-446.

Payton, M. and Hartley, B., "Mutants of Bacillus stearothermophilus lacking NAD-linked L-lactate dehydrogenase," FEMS Microbiology Letters, vol. 26, 1985, pp. 333-336.

Amartey, S., Leak, D., and Hartley, B., "Development and Optimization of a Defined Medium for Aerobic Growth of Bacillus stearothermophilus LLD-15," Biotechnology Letters, vol. 13, 1991, 621-626.

Danner, H., et al., "Bacillus stearothermophilus for Thermophilic Production of L-Lactic Acid," Applied Biochemistry and Biotechnology, vol. 70-72, 1998, pp. 895-903.

Rao, J., and Satyanarayana, T., "Hyperthermostable, $Ca^{2+}$-Independent, and High Maltose-Forming α-Amylase Production by an Extreme Thermophile Geobacillus thermoleovorans: Whole Cell Immobilization," Applied Biochemistry and Biotechnology, vol. 159, 2009, pp. 464-477.

Tang, Y., et al., "Analysis of Metabolic Pathways and Fluxes in a Newly Discovered Thermophilic and Ethanol-Tolerant Geobacillus Strain," Biotechnology and Engineering, 2008, 10 pages.

Suzuki, Y., et al., "*Bacillus thermoglucosidasius* sp. nov., a New Species of Obligately Thermophilic Bacilli," Systematic and Applied Microbiology, vol. 4, 1983, pp. 487-495.

Coorevits, A., et al., "Taxonomic revision of the genus *Geobacillus*," International Journal of Systematic and Evolutionary Microbiology, vol. 62, 2012, pp. 1470-1485.

Suzuki, Y., Kishigami, T., and Abe, S., "Production of Extracellular α-Glucosidase by a Thermophilic Bacillus Species," Applied and Environmental Microbiology, vol. 31, 1976, pp. 807-812.

Fong, N., et al., "Isolation and characterization of two novel ethanol-tolerant facultative-anaerobic thermophilic bacteria strains from waste compost," Extremophiles, vol. 10, 2006, pp. 363-372.

Grabar, T., et al. "Methylglyoxal bypass identified as source of chiral contamination in L(+) and D(−)-lactate fermentations by recombinant *Escherichia coli*," Biotechnology Letters, vol. 28, 2006, 9 pages.

(Continued)

*Primary Examiner* — Suzanne M Noakes
(74) *Attorney, Agent, or Firm* — Oliff PLC

(57) ABSTRACT

A genetically engineered thermophilic bacterial cell that is facultative anaerobic and (S)-lactic acid producing including inactivation or deletion of the endogenous methylglyoxal synthase gene mgsA.

14 Claims, No Drawings
Specification includes a Sequence Listing.

(56) References Cited

OTHER PUBLICATIONS

Gaballa, A., et al., "Biosynthesis and functions of bacillithiol, a major low-molecular-weight thiol in Bacilli," Proceedings of the National Academy of Sciences of the United States of America, vol. 107, 2010, pp. 6482-6486, with supporting information—19 pages.

Helmann, John D., "Bacillithiol, a New Player in Bacterial Redox Homeostasis," Antioxidants and Redox Signaling, vol. 15, 2011, pp. 123-133.

Chandrangsu, P., et al., "Methylglyoxal resistance in Bacillus subtilis: contributions of bacillithiol-dependent and independent pathways," Molecular Microbiology, vol. 91, 2014, pp. 706-715.

Zhu Jiangfeng and Shimizu, Kazuyuki, "Effect of a single-gene knockout on the metabolic regulation in Escherichia coli for D-lactate production under microaerobic condition," Metabolic Engineering, vol. 7, 2005, pp. 104-115.

Zhou, S., Shanmugam, K., and Ingram, L., "Functional Replacement of the Escherichia coli D-(−)-Lactate Dehydrogenase Gene (IdhA) with the L-(+)-Lactate Dehydrogenase Gene (IdhL) from Pediococcus acidilactici," Applied and Environmental Microbiology, vol. 69, 2003, pp. 2237-2244.

Liu, H. et al., "Production of Lactate in Escherichia coli by Redox Regulation Genetically and Physiologically," Applied Biochemistry and Biotechnology, vol. 164, 2011, pp. 162-169.

Beyer, L., et al., "Coordination of FocA and Pyruvate Formate-Lyase Synthesis in Escherichia coli Demonstrates Preferential Translocation of Formate over Other Mixed-Acid Fermentation Products," Journal of Bacteriology, vol. 195, 2013, pp. 1428-1435.

Catalanotti, et al., "Altered Fermentative Metabolism in Chlamydomonas reinhardtii Mutants Lacking Pyruvate Formate Lyase and Both Pyruvate Formate Lyase and Alcohol Dehydrogenase," The Plant Cell, vol. 24, 2012, pp. 692-707, with supplemental data—5 pages.

Gonzy-Treboul, G., Karmazyn-Campelli, C., and Stragier, P., "Developmental Regulation of Transcription of the Bacillus subtilis ftsAZ Operon," J. Mol. Biol., vol. 224, 1992, 967-979.

Fleming, A. et al., "Extracellular Enzyme Synthesis in a Sporulation-Deficient Strain of Bacillus licheniformis," Applied and Environmental Microbiology, vol. 61, 1995, pp. 3775-3780.

Wang, J., Greenhut, W., and Shih, J., "Development of an asporogenic Bacillus licheniformis for the production of keratinase," Journal of Applied Microbiology, vol. 98, 2005, pp. 761-767.

Kovacs, A. et al., "Genetic Tool Development for a New Host for Biotechnology, the Thermotolerant Bacterium Bacillus coagulans," Applied and Environmental Microbiology, vol. 76, 2010, pp. 4085-4088.

Taylor, M., Esteban, C., and Leak, D., "Development of a versatile shuttle vector for gene expression in Geobacillus spp.," Plasmid, vol. 60, 2008, pp. 45-52.

Cripps, R., et al., "Metabolic engineering of Geobacillus thermoglucosidasius for high yield ethanol production," Metabolic Engineering, vol. 11, 2009, 11 pages.

Mazumdar, S. et al. "Efficient synthesis of L-lactic acid from glycerol by metabolically engineered Escherichia coli," Microbial Cell Factories, vol. 12, 2013, 11 pages.

Oct. 27, 2015 International Search Report for Application No. PCT/EP2015/065995.

Oct. 27, 2015 Written Opinion for Application No. PCT/EP2015/065995.

Sep. 25, 2017 Office Action issued in Australian Patent Application No. 2015294138.

Feb. 14, 2018 Office Action issued in Russian Patent Application No. 2017102895.

Feb. 14, 2018 Search Report issued in Russian Patent Application No. 2017102895.

Mar. 14, 2018 Office Action issued in Japanse Patent Application No. 2017-502623.

Apr. 4, 2018 Office Action issued in European Patent Application No. 15 738 320.9.

Yomano, L. P. et al., "Deletion of methylglyoxal synthase gene (mgsA) increased sugar co-metabolism in ethanol-producing Escherichia coli," Biotechnol Lett, vol. 31, 2009, 11 pages.

Flores, A. et al., "Natural Variation in the Promoter of the Gene Encoding the Mga Regulator Alters Host-Pathogen Interactions in Group A Streptococcus Carrier Strains," Infection and Immunity, 2013, vol. 81, 10 pages.

May 25, 2018 Office Action issued in Korean Patent Application No. 10-2017-7004576.

Jul. 3, 2018 Office Action issued in Ukrainian Patent Application No. A201700514.

Database UniProtKB/Swiss-Prot; Accession No. C5D3B8; http://www.uniprot.org/uniprot/C5D3B8.txt?version=1; Jul. 28, 2009.

Oct. 22, 2018 Partial Translation of Office Action issued in Japanese Patent Application No. 2017-502623.

* cited by examiner

SEQUENCE LISTING

<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
tcgccttctt ctgtgtcatc         20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2

```
ctggaggaga gcaatgaaac                                               20

<210> SEQ ID NO 3
<211> LENGTH: 32
<212> TYPE: DNA
<213> ORGANISM: Artificial Sequence
<220> FEATURE:
<223> OTHER INFORMATION: Synthetic primer

<400> SEQUENCE: 3
gcgcgggtac ccagcaaacc gagcggaatc ag                                 32

<210> SEQ ID NO 4
<211> LENGTH: 31
<212> TYPE: DNA
<213> ORGANISM: Artificial Sequence
<220> FEATURE:
<223> OTHER INFORMATION: Synthetic primer

<400> SEQUENCE: 4
gcgcggtcga cggatgggta ggcatccatt c                                  31

<210> SEQ ID NO 5
<211> LENGTH: 33
<212> TYPE: DNA
<213> ORGANISM: Artificial Sequence
<220> FEATURE:
<223> OTHER INFORMATION: Synthetic primer

<400> SEQUENCE: 5
gcgcggtcga cgtctcccctt agttacataa cgc                               33

<210> SEQ ID NO 6
<211> LENGTH: 32
<212> TYPE: DNA
<213> ORGANISM: Artificial Sequence
<220> FEATURE:
<223> OTHER INFORMATION: Synthetic primer

<400> SEQUENCE: 6
gcgcgaagct tgcttcgcag tccaatcgtc gc                                 32

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
gctaagatcg gccatacgtt aagc                                          24

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
ggagacgagc ttggcgtcct g                                             21

<210> SEQ ID NO 9
<211> LENGTH: 28
<212> TYPE: DNA
```

```
<213> ORGANISM: Artificial Sequence
<220> FEATURE:
<223> OTHER INFORMATION: Synthetic primer

<400> SEQUENCE: 9
gccctcgaga gggctcgcct ttgggaag                                        28

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
gctcgttata gtcgatcggt tc                                              22

<210> SEQ ID NO 11
<211> LENGTH: 33
<212> TYPE: DNA
<213> ORGANISM: Artificial Sequence
<220> FEATURE:
<223> OTHER INFORMATION: Synthetic primer

<400> SEQUENCE: 11
gcgcgggatc cgctttccgt tgccatttg ccg                                   33

<210> SEQ ID NO 12
<211> LENGTH: 35
<212> TYPE: DNA
<213> ORGANISM: Artificial Sequence
<220> FEATURE:
<223> OTHER INFORMATION: Synthetic primer

<400> SEQUENCE: 12
gcgcgctgca gggcaagact gacagaagag cttgg                                35

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
cagcagtaac ggcatccgat tg                                              22

<210> SEQ ID NO 14
<211> LENGTH: 27
<212> TYPE: DNA
<213> ORGANISM: Artificial Sequence
<220> FEATURE:
<223> OTHER INFORMATION: Synthetic primer

<400> SEQUENCE: 14
gcggatatga ttgaatttgt gactgcc                                         27

<210> SEQ ID NO 15
<211> LENGTH: 33
<212> TYPE: DNA
<213> ORGANISM: Artificial Sequence
<220> FEATURE:
<223> OTHER INFORMATION: Synthetic primer

<400> SEQUENCE: 15
tatgcgacgg gcgcgtggag gaatattgtc cgc                                  33
```

<210> SEQ ID NO 16
<211> LENGTH: 36
<212> TYPE: DNA
<213> ORGANISM: Artificial Sequence
<220> FEATURE:
<223> OTHER INFORMATION: Synthetic primer

<400> SEQUENCE: 16
attcctccac gcgcccgtcg catacagttc atgttg                                36

<210> SEQ ID NO 17
<211> LENGTH: 33
<212> TYPE: DNA
<213> ORGANISM: Artificial Sequence
<220> FEATURE:
<223> OTHER INFORMATION: Synthetic primer

<400> SEQUENCE: 17
gcgcgggatc ccccaaatgg cattaccggt gtg                                   33

<210> SEQ ID NO 18
<211> LENGTH: 34
<212> TYPE: DNA
<213> ORGANISM: Artificial Sequence
<220> FEATURE:
<223> OTHER INFORMATION: Synthetic primer

<400> SEQUENCE: 18
tgttattgct ggcagtttcc ctcccatgca tctg                                  34

<210> SEQ ID NO 19
<211> LENGTH: 35
<212> TYPE: DNA
<213> ORGANISM: Artificial Sequence
<220> FEATURE:
<223> OTHER INFORMATION: Synthetic primer

<400> SEQUENCE: 19
ggagggaaac tgccagcaat aacaccaaca ggctc                                 35

<210> SEQ ID NO 20
<211> LENGTH: 34
<212> TYPE: DNA
<213> ORGANISM: Artificial Sequence
<220> FEATURE:
<223> OTHER INFORMATION: Synthetic sequence

<400> SEQUENCE: 20
gcgcgctgca gcgaaagcga acgaaattgc caac                                  34

<210> SEQ ID NO 21
<211> LENGTH: 24
<212> TYPE: DNA
<213> ORGANISM: Artificial Sequence
<220> FEATURE:
<223> OTHER INFORMATION: Synthetic primer

<400> SEQUENCE: 21
gccaagatgg atatgggcgt tagc                                             24

<210> SEQ ID NO 22
<211> LENGTH: 22
<212> TYPE: DNA
<213> ORGANISM: Artificial Sequence
<220> FEATURE:

<223> OTHER INFORMATION: Synthetic primer

<400> SEQUENCE: 22
ccggagatgg acggaattga ag    22

<210> SEQ ID NO 23
<211> LENGTH: 423
<212> TYPE: DNA
<213> ORGANISM: Geobacillus thermoglucosidans
<220> FEATURE:
<221> NAME/KEY: CDS
<222> LOCATION: (1)..(423)

<400> SEQUENCE: 23

```
gtg aga atc gcg ttg atc gcg cat gat aaa aag aaa gcg gat atg att    48
Val Arg Ile Ala Leu Ile Ala His Asp Lys Lys Lys Ala Asp Met Ile
1               5                   10                  15 gaa ttt gtg act gcc tat cag ccg att tta gaa caa cat gaa ctg tat    96
Glu Phe Val Thr Ala Tyr Gln Pro Ile Leu Glu Gln His Glu Leu Tyr
                20                  25                  30 gcg acg ggc acg acc ggc ttg cgc att cag gaa gcg aca gga ctg ccg    144
Ala Thr Gly Thr Thr Gly Leu Arg Ile Gln Glu Ala Thr Gly Leu Pro
            35                  40                  45 gtg cat cgc ttt caa tcg ggg cca tat ggc ggc gat caa gaa att ggt    192
Val His Arg Phe Gln Ser Gly Pro Tyr Gly Gly Asp Gln Glu Ile Gly
        50                  55                  60 gca atg att gcc cgc aat gaa atg gat atg gtg ata ttt ttc cgc gat    240
Ala Met Ile Ala Arg Asn Glu Met Asp Met Val Ile Phe Phe Arg Asp
65                  70                  75                  80 ccg ttg acg gca cag ccg cat gag ccg gat gtc agt gcg ctc att cgc    288
Pro Leu Thr Ala Gln Pro His Glu Pro Asp Val Ser Ala Leu Ile Arg
                85                  90                  95 tta tgt gat gtc tat tcc gtg ccg ctt gca acc aat atg ggg acg gcg    336
Leu Cys Asp Val Tyr Ser Val Pro Leu Ala Thr Asn Met Gly Thr Ala
            100                 105                 110 gaa att tta att aaa ggg ctg gag cgc ggc gat ttt gcg tgg agg aat    384
Glu Ile Leu Ile Lys Gly Leu Glu Arg Gly Asp Phe Ala Trp Arg Asn
        115                 120                 125 att gtc cgc ggc cga aaa ggt gag aca aat gga ata taa    423
Ile Val Arg Gly Arg Lys Gly Glu Thr Asn Gly Ile
    130                 135                 140
```

<210> SEQ ID NO 24
<211> LENGTH: 140
<212> TYPE: PRT
<213> ORGANISM: Geobacillus thermoglucosidans

<400> SEQUENCE: 24

```
Val Arg Ile Ala Leu Ile Ala His Asp Lys Lys Lys Ala Asp Met Ile
1               5                   10                  15

Glu Phe Val Thr Ala Tyr Gln Pro Ile Leu Glu Gln His Glu Leu Tyr
                20                  25                  30

Ala Thr Gly Thr Thr Gly Leu Arg Ile Gln Glu Ala Thr Gly Leu Pro
            35                  40                  45

Val His Arg Phe Gln Ser Gly Pro Tyr Gly Gly Asp Gln Glu Ile Gly
        50                  55                  60

Ala Met Ile Ala Arg Asn Glu Met Asp Met Val Ile Phe Phe Arg Asp
65                  70                  75                  80

Pro Leu Thr Ala Gln Pro His Glu Pro Asp Val Ser Ala Leu Ile Arg
                85                  90                  95
```

```
Leu Cys Asp Val Tyr Ser Val Pro Leu Ala Thr Asn Met Gly Thr Ala
                100                 105                 110
Glu Ile Leu Ile Lys Gly Leu Glu Arg Gly Asp Phe Ala Trp Arg Asn
            115                 120                 125
Ile Val Arg Gly Arg Lys Gly Glu Thr Asn Gly Ile
        130                 135                 140

<210> SEQ ID NO 25
<211> LENGTH: 2250
<212> TYPE: DNA
<213> ORGANISM: Geobacillus thermoglucosidans
<220> FEATURE:
<221> NAME/KEY: CDS
<222> LOCATION: (1)..(2250)

<400> SEQUENCE: 25 atg aaa caa gcc act gtt gta ttg gac cct tgg cgc aat ttt aaa ggg        48
Met Lys Gln Ala Thr Val Val Leu Asp Pro Trp Arg Asn Phe Lys Gly
1               5                   10                  15 tca aaa tgg aaa aaa tcg att gac gtc cgt gat ttt att tta aac aat        96
Ser Lys Trp Lys Lys Ser Ile Asp Val Arg Asp Phe Ile Leu Asn Asn
            20                  25                  30 gta acc gtt tac tac ggg gat gaa tca ttc cta gaa ggg cct aca gaa       144
Val Thr Val Tyr Tyr Gly Asp Glu Ser Phe Leu Glu Gly Pro Thr Glu
        35                  40                  45 gca acg aaa aaa cta tgg gaa caa gtg atg gaa ttg tcg aaa caa gaa       192
Ala Thr Lys Lys Leu Trp Glu Gln Val Met Glu Leu Ser Lys Gln Glu
    50                  55                  60 cgc gaa aaa ggc ggc gtc ctt gat atg gac aca tcg att gtt tcg acc       240
Arg Glu Lys Gly Gly Val Leu Asp Met Asp Thr Ser Ile Val Ser Thr
65                  70                  75                  80 atc act tcc cac gga cca ggt tat tta aac aaa gac ttg gaa aaa atc       288
Ile Thr Ser His Gly Pro Gly Tyr Leu Asn Lys Asp Leu Glu Lys Ile
                85                  90                  95 gta ggt ttt caa aca gat aaa ccg ttt aag cgt gca tta atg ccg ttt       336
Val Gly Phe Gln Thr Asp Lys Pro Phe Lys Arg Ala Leu Met Pro Phe
            100                 105                 110 ggc ggc att cgc atg gcg caa caa tca tgc gaa gca tac ggt tac aaa       384
Gly Gly Ile Arg Met Ala Gln Gln Ser Cys Glu Ala Tyr Gly Tyr Lys
        115                 120                 125 gta agc gac gaa gtg aaa aaa atc ttt acg gaa tac cgg aaa aca cac       432
Val Ser Asp Glu Val Lys Lys Ile Phe Thr Glu Tyr Arg Lys Thr His
    130                 135                 140 aac caa ggt gtg ttt gac gtt tac acc gac gag atg aga tta gcg cgc       480
Asn Gln Gly Val Phe Asp Val Tyr Thr Asp Glu Met Arg Leu Ala Arg
145                 150                 155                 160 aaa gca gga atc atc acc ggc ctt cct gat gcg tac gga cgc ggc cgt       528
Lys Ala Gly Ile Ile Thr Gly Leu Pro Asp Ala Tyr Gly Arg Gly Arg
                165                 170                 175 atc atc ggc gac tat cgt cgc gtc gcg tta tac ggt gtc gat cgt ttg       576
Ile Ile Gly Asp Tyr Arg Arg Val Ala Leu Tyr Gly Val Asp Arg Leu
            180                 185                 190 atc gaa gaa aaa caa aaa gat ttg aaa aac act ggc gca aga acg atg       624
Ile Glu Glu Lys Gln Lys Asp Leu Lys Asn Thr Gly Ala Arg Thr Met
        195                 200                 205 acc gaa gac att atc cgt ctt cgc gaa gaa att tca gag caa att cgc       672
Thr Glu Asp Ile Ile Arg Leu Arg Glu Glu Ile Ser Glu Gln Ile Arg
    210                 215                 220 gca tta aac gag tta aaa caa atg gcg tta agc tat gga tat gat att       720
Ala Leu Asn Glu Leu Lys Gln Met Ala Leu Ser Tyr Gly Tyr Asp Ile
225                 230                 235                 240
```

```
tcc aaa ccg gca cgg aac gca cat gaa gca ttc caa tgg ctc tat ttc      768
Ser Lys Pro Ala Arg Asn Ala His Glu Ala Phe Gln Trp Leu Tyr Phe
            245                 250                 255 gct tat ctt gct gct att aaa gaa caa aac ggc gcg gcg atg agc tta      816
Ala Tyr Leu Ala Ala Ile Lys Glu Gln Asn Gly Ala Ala Met Ser Leu
        260                 265                 270 ggg cgc gtt tcc acc ttc ttg gat att tat atc gag cgc gac ttt gca      864
Gly Arg Val Ser Thr Phe Leu Asp Ile Tyr Ile Glu Arg Asp Phe Ala
    275                 280                 285 gaa ggc aca tta acg gaa aaa gaa gcg caa gaa ctt gtc gac cat ttt      912
Glu Gly Thr Leu Thr Glu Lys Glu Ala Gln Glu Leu Val Asp His Phe
290                 295                 300 gtg atg aaa ttg cgc ctt gtc aaa ttt gcc aga acg ccg gaa tat aac      960
Val Met Lys Leu Arg Leu Val Lys Phe Ala Arg Thr Pro Glu Tyr Asn
305                 310                 315                 320 gaa ctg ttt agc gga gac ccg aca tgg gtt acc gaa tcg atc ggc gga     1008
Glu Leu Phe Ser Gly Asp Pro Thr Trp Val Thr Glu Ser Ile Gly Gly
            325                 330                 335 att gcc att gat ggc cgt ccg tta gtg aca aag aac tcg ttc cgt ttc     1056
Ile Ala Ile Asp Gly Arg Pro Leu Val Thr Lys Asn Ser Phe Arg Phe
        340                 345                 350 ctt cat acg tta gat aac tta gga cct gcg cca gag cca aac tta aca     1104
Leu His Thr Leu Asp Asn Leu Gly Pro Ala Pro Glu Pro Asn Leu Thr
    355                 360                 365 gta ctt tgg tcg aaa caa ttg ccg gaa gca ttc aaa gag tat tgc gcg     1152
Val Leu Trp Ser Lys Gln Leu Pro Glu Ala Phe Lys Glu Tyr Cys Ala
370                 375                 380 aaa atg tcg atc aaa aca agc tcg att caa tat gaa aat gac gac tta     1200
Lys Met Ser Ile Lys Thr Ser Ser Ile Gln Tyr Glu Asn Asp Asp Leu
385                 390                 395                 400 atg cgc gtc gaa ttt ggc gat gat tac gga att gct tgc tgc gta tca     1248
Met Arg Val Glu Phe Gly Asp Asp Tyr Gly Ile Ala Cys Cys Val Ser
            405                 410                 415 gcg atg cga atc ggc aaa caa atg caa ttt ttc gga gcg cgc gcc aac     1296
Ala Met Arg Ile Gly Lys Gln Met Gln Phe Phe Gly Ala Arg Ala Asn
        420                 425                 430 ctc gcc aaa gca ttg tta tat gcg att aac ggc ggc gtc gat gaa aaa     1344
Leu Ala Lys Ala Leu Leu Tyr Ala Ile Asn Gly Gly Val Asp Glu Lys
    435                 440                 445 ttg aaa atc caa gtt ggc cct gaa ttt gcg ccg att acc tcc gaa tat     1392
Leu Lys Ile Gln Val Gly Pro Glu Phe Ala Pro Ile Thr Ser Glu Tyr
450                 455                 460 tta aat tat gat gaa gtg atg cat aaa ttc gat caa gtg ctt gaa tgg     1440
Leu Asn Tyr Asp Glu Val Met His Lys Phe Asp Gln Val Leu Glu Trp
465                 470                 475                 480 ctt gcc gaa ctt tat att aac aca ctg aat gtc atc cat tac atg cac     1488
Leu Ala Glu Leu Tyr Ile Asn Thr Leu Asn Val Ile His Tyr Met His
            485                 490                 495 gac aaa tat tgt tat gaa cgc att gaa atg gcg ctt cac gat act cac     1536
Asp Lys Tyr Cys Tyr Glu Arg Ile Glu Met Ala Leu His Asp Thr His
        500                 505                 510 gtt tta cgc aca atg gcc act ggc att gcc gga ttg tca gtt gtc gtc     1584
Val Leu Arg Thr Met Ala Thr Gly Ile Ala Gly Leu Ser Val Val Val
    515                 520                 525 gat tcg tta agc gcg atc aaa tat gca aaa gtc aaa ccg atc cgc gat     1632
Asp Ser Leu Ser Ala Ile Lys Tyr Ala Lys Val Lys Pro Ile Arg Asp
530                 535                 540 gaa aac ggc att gct gtt gat ttt gaa atg gaa ggc gac ttc ccg aaa     1680
Glu Asn Gly Ile Ala Val Asp Phe Glu Met Glu Gly Asp Phe Pro Lys
```

```
                545                 550                 555                 560
tac gga aat aac gat gat cgc gtc gac caa att gcc gtt gat tta gtc     1728
Tyr Gly Asn Asn Asp Asp Arg Val Asp Gln Ile Ala Val Asp Leu Val
                    565                 570                 575 gaa cgt ttt atg acg aaa ttg aaa aaa cat aaa aca tat cgc gat tcg     1776
Glu Arg Phe Met Thr Lys Leu Lys Lys His Lys Thr Tyr Arg Asp Ser
                580                 585                 590 aaa cat acg cta tct att tta aca att acg tct aac gtt gta tac ggg     1824
Lys His Thr Leu Ser Ile Leu Thr Ile Thr Ser Asn Val Val Tyr Gly
            595                 600                 605 aaa aag acc gga aat aca cca gat ggc cgc cgc gct ggc gaa ccg ttt     1872
Lys Lys Thr Gly Asn Thr Pro Asp Gly Arg Arg Ala Gly Glu Pro Phe
        610                 615                 620 gcc cca gga gca aac ccg ttg cac ggc gtc gac acg aaa gga gcg ctc     1920
Ala Pro Gly Ala Asn Pro Leu His Gly Val Asp Thr Lys Gly Ala Leu
625                 630                 635                 640 gct tcg cta agc tct gtc gcg aaa tta cca tat gaa cat gca tta gat     1968
Ala Ser Leu Ser Ser Val Ala Lys Leu Pro Tyr Glu His Ala Leu Asp
                645                 650                 655 ggc att tcg aat acg ttc tcg atc gtg ccg aaa gcg tta gga aaa gag     2016
Gly Ile Ser Asn Thr Phe Ser Ile Val Pro Lys Ala Leu Gly Lys Glu
            660                 665                 670 gaa gga gac cgt gtc cgc aac ctt gtc gcc gtt tta gac gga tac atg     2064
Glu Gly Asp Arg Val Arg Asn Leu Val Ala Val Leu Asp Gly Tyr Met
        675                 680                 685 gaa aaa ggc ggg cat cat ctc aac att aac gtg ttg aac cgc gaa aca     2112
Glu Lys Gly Gly His His Leu Asn Ile Asn Val Leu Asn Arg Glu Thr
    690                 695                 700 ttg tta gat gcg atg gaa cat cca gaa aaa tat ccg caa tta acg att     2160
Leu Leu Asp Ala Met Glu His Pro Glu Lys Tyr Pro Gln Leu Thr Ile
705                 710                 715                 720 cgc gtt tct gga tat gcc gtc aac ttc ata aaa tta acg cgc gaa caa     2208
Arg Val Ser Gly Tyr Ala Val Asn Phe Ile Lys Leu Thr Arg Glu Gln
                725                 730                 735 caa atc gat gtc att aac cgc acg ttc cac gaa acg atg taa             2250
Gln Ile Asp Val Ile Asn Arg Thr Phe His Glu Thr Met
            740                 745
```

<210> SEQ ID NO 26
<211> LENGTH: 749
<212> TYPE: PRT
<213> ORGANISM: Geobacillus thermoglucosidans

<400> SEQUENCE: 26

```
Met Lys Gln Ala Thr Val Val Leu Asp Pro Trp Arg Asn Phe Lys Gly
1               5                   10                  15

Ser Lys Trp Lys Lys Ser Ile Asp Val Arg Asp Phe Ile Leu Asn Asn
            20                  25                  30

Val Thr Val Tyr Tyr Gly Asp Glu Ser Phe Leu Glu Gly Pro Thr Glu
        35                  40                  45

Ala Thr Lys Lys Leu Trp Glu Gln Val Met Glu Leu Ser Lys Gln Glu
    50                  55                  60

Arg Glu Lys Gly Gly Val Leu Asp Met Asp Thr Ser Ile Val Ser Thr
65                  70                  75                  80

Ile Thr Ser His Gly Pro Gly Tyr Leu Asn Lys Asp Leu Glu Lys Ile
                85                  90                  95

Val Gly Phe Gln Thr Asp Lys Pro Phe Lys Arg Ala Leu Met Pro Phe
            100                 105                 110
```

Gly Gly Ile Arg Met Ala Gln Gln Ser Cys Glu Ala Tyr Gly Tyr Lys
            115                 120                 125

Val Ser Asp Glu Val Lys Lys Ile Phe Thr Glu Tyr Arg Lys Thr His
130                 135                 140

Asn Gln Gly Val Phe Asp Val Tyr Thr Asp Glu Met Arg Leu Ala Arg
145                 150                 155                 160

Lys Ala Gly Ile Ile Thr Gly Leu Pro Asp Ala Tyr Gly Arg Gly Arg
                165                 170                 175

Ile Ile Gly Asp Tyr Arg Arg Val Ala Leu Tyr Gly Val Asp Arg Leu
            180                 185                 190

Ile Glu Glu Lys Gln Lys Asp Leu Lys Asn Thr Gly Ala Arg Thr Met
        195                 200                 205

Thr Glu Asp Ile Ile Arg Leu Arg Glu Glu Ile Ser Glu Gln Ile Arg
    210                 215                 220

Ala Leu Asn Glu Leu Lys Gln Met Ala Leu Ser Tyr Gly Tyr Asp Ile
225                 230                 235                 240

Ser Lys Pro Ala Arg Asn Ala His Glu Ala Phe Gln Trp Leu Tyr Phe
                245                 250                 255

Ala Tyr Leu Ala Ala Ile Lys Glu Gln Asn Gly Ala Ala Met Ser Leu
            260                 265                 270

Gly Arg Val Ser Thr Phe Leu Asp Ile Tyr Ile Glu Arg Asp Phe Ala
        275                 280                 285

Glu Gly Thr Leu Thr Glu Lys Glu Ala Gln Glu Leu Val Asp His Phe
    290                 295                 300

Val Met Lys Leu Arg Leu Val Lys Phe Ala Arg Thr Pro Glu Tyr Asn
305                 310                 315                 320

Glu Leu Phe Ser Gly Asp Pro Thr Trp Val Thr Glu Ser Ile Gly Gly
                325                 330                 335

Ile Ala Ile Asp Gly Arg Pro Leu Val Thr Lys Asn Ser Phe Arg Phe
            340                 345                 350

Leu His Thr Leu Asp Asn Leu Gly Pro Ala Pro Glu Pro Asn Leu Thr
        355                 360                 365

Val Leu Trp Ser Lys Gln Leu Pro Glu Ala Phe Lys Glu Tyr Cys Ala
    370                 375                 380

Lys Met Ser Ile Lys Thr Ser Ser Ile Gln Tyr Glu Asn Asp Asp Leu
385                 390                 395                 400

Met Arg Val Glu Phe Gly Asp Asp Tyr Gly Ile Ala Cys Cys Val Ser
                405                 410                 415

Ala Met Arg Ile Gly Lys Gln Met Gln Phe Phe Gly Ala Arg Ala Asn
            420                 425                 430

Leu Ala Lys Ala Leu Leu Tyr Ala Ile Asn Gly Gly Val Asp Glu Lys
        435                 440                 445

Leu Lys Ile Gln Val Gly Pro Glu Phe Ala Pro Ile Thr Ser Glu Tyr
    450                 455                 460

Leu Asn Tyr Asp Glu Val Met His Lys Phe Asp Gln Val Leu Glu Trp
465                 470                 475                 480

Leu Ala Glu Leu Tyr Ile Asn Thr Leu Asn Val Ile His Tyr Met His
                485                 490                 495

Asp Lys Tyr Cys Tyr Glu Arg Ile Glu Met Ala Leu His Asp Thr His
            500                 505                 510

Val Leu Arg Thr Met Ala Thr Gly Ile Ala Gly Leu Ser Val Val Val
        515                 520                 525

Asp Ser Leu Ser Ala Ile Lys Tyr Ala Lys Val Lys Pro Ile Arg Asp

```
                530                 535                 540
Glu Asn Gly Ile Ala Val Asp Phe Glu Met Glu Gly Asp Phe Pro Lys
545                 550                 555                 560

Tyr Gly Asn Asn Asp Asp Arg Val Asp Gln Ile Ala Val Asp Leu Val
                565                 570                 575

Glu Arg Phe Met Thr Lys Leu Lys His Lys Thr Tyr Arg Asp Ser
                580                 585                 590

Lys His Thr Leu Ser Ile Leu Thr Ile Thr Ser Asn Val Val Tyr Gly
                595                 600                 605

Lys Lys Thr Gly Asn Thr Pro Asp Gly Arg Arg Ala Gly Glu Pro Phe
                610                 615                 620

Ala Pro Gly Ala Asn Pro Leu His Gly Arg Asp Thr Lys Gly Ala Leu
625                 630                 635                 640

Ala Ser Leu Ser Ser Val Ala Lys Leu Pro Tyr Glu His Ala Leu Asp
                645                 650                 655

Gly Ile Ser Asn Thr Phe Ser Ile Val Pro Lys Ala Leu Gly Lys Glu
                660                 665                 670

Glu Gly Asp Arg Val Arg Asn Leu Val Ala Val Leu Asp Gly Tyr Met
                675                 680                 685

Glu Lys Gly Gly His His Leu Asn Ile Asn Val Leu Asn Arg Glu Thr
                690                 695                 700

Leu Leu Asp Ala Met Glu His Pro Glu Lys Tyr Pro Gln Leu Thr Ile
705                 710                 715                 720

Arg Val Ser Gly Tyr Ala Val Asn Phe Ile Lys Leu Thr Arg Glu Gln
                725                 730                 735

Gln Ile Asp Val Ile Asn Arg Thr Phe His Glu Thr Met
                740                 745

<210> SEQ ID NO 27
<211> LENGTH: 750
<212> TYPE: DNA
<213> ORGANISM: Geobacillus thermoglucosidans
<220> FEATURE:
<221> NAME/KEY: CDS
<222> LOCATION: (1)..(750)

<400> SEQUENCE: 27 atg aaa gga ttt att cat tcc atc gaa tca tgc ggc acc gtc gac ggg    48
Met Lys Gly Phe Ile His Ser Ile Glu Ser Cys Gly Thr Val Asp Gly
1               5                   10                  15 ccg ggc ctt cgc tat gtc atc ttt aca caa ggc tgt gtg ctg cgc tgc    96
Pro Gly Leu Arg Tyr Val Ile Phe Thr Gln Gly Cys Val Leu Arg Cys
            20                  25                  30 caa tat tgc cat aac gcc gat acg tgg gaa att gga aaa gga aaa gaa   144
Gln Tyr Cys His Asn Ala Asp Thr Trp Glu Ile Gly Lys Gly Lys Glu
        35                  40                  45 atg act gtg gaa gaa atc atc gat gac gtg aaa aca tac ttg ccg ttt   192
Met Thr Val Glu Glu Ile Ile Asp Asp Val Lys Thr Tyr Leu Pro Phe
    50                  55                  60 atc aac gct tcc aat ggc gga att acc gtc agc ggc gga gag cct ttg   240
Ile Asn Ala Ser Asn Gly Gly Ile Thr Val Ser Gly Gly Glu Pro Leu
65                  70                  75                  80 tta caa atc gat ttt tta att gaa tta ttt aaa gca tgc aaa aaa ctg   288
Leu Gln Ile Asp Phe Leu Ile Glu Leu Phe Lys Ala Cys Lys Lys Leu
                85                  90                  95 ggc att cat acc gcg atc gat tca tcg gga gga tgc tac acg acg gaa   336
Gly Ile His Thr Ala Ile Asp Ser Ser Gly Gly Cys Tyr Thr Thr Glu
            100                 105                 110
```

```
gca tcg ttc cag caa aaa tta aat gaa tta ctt tcc tat acc gat tta      384
Ala Ser Phe Gln Gln Lys Leu Asn Glu Leu Leu Ser Tyr Thr Asp Leu
        115                 120                 125 att ttg ctt gat tta aaa cat atc gat gag aaa aaa cac cgg aaa ctg      432
Ile Leu Leu Asp Leu Lys His Ile Asp Glu Lys Lys His Arg Lys Leu
130                 135                 140 aca gga aaa acc aat aaa cat att tta caa ttt gct cag ttt tta tcc      480
Thr Gly Lys Thr Asn Lys His Ile Leu Gln Phe Ala Gln Phe Leu Ser
145                 150                 155                 160 gaa aaa aac gtt cct gtt tgg atc cgg cat gtt ctc gtt cca acc atc      528
Glu Lys Asn Val Pro Val Trp Ile Arg His Val Leu Val Pro Thr Ile
                165                 170                 175 aca gac gac ccg aat gac ttg cgc cgt ctc gcc gct ttt att cgc aca      576
Thr Asp Asp Pro Asn Asp Leu Arg Arg Leu Ala Ala Phe Ile Arg Thr
            180                 185                 190 tta aag aat gtg aaa aaa att gaa att ctc cca tac cat aaa tta gga      624
Leu Lys Asn Val Lys Lys Ile Glu Ile Leu Pro Tyr His Lys Leu Gly
        195                 200                 205 gta tac aaa tgg aaa gcg ctt gga tta aaa tac cct ttg gaa gga atc      672
Val Tyr Lys Trp Lys Ala Leu Gly Leu Lys Tyr Pro Leu Glu Gly Ile
    210                 215                 220 gag cct cct tcg gaa gaa agc gta caa atg gca cag cga att ctt aac      720
Glu Pro Pro Ser Glu Glu Ser Val Gln Met Ala Gln Arg Ile Leu Asn
225                 230                 235                 240 gga aca gaa gat aca gta tct ctt gcg taa                              750
Gly Thr Glu Asp Thr Val Ser Leu Ala
                245

<210> SEQ ID NO 28
<211> LENGTH: 249
<212> TYPE: PRT
<213> ORGANISM: Geobacillus thermoglucosidans

<400> SEQUENCE: 28

Met Lys Gly Phe Ile His Ser Ile Glu Ser Cys Gly Thr Val Asp Gly
1               5                   10                  15

Pro Gly Leu Arg Tyr Val Ile Phe Thr Gln Gly Cys Val Leu Arg Cys
            20                  25                  30

Gln Tyr Cys His Asn Ala Asp Thr Trp Glu Ile Gly Lys Gly Lys Glu
        35                  40                  45

Met Thr Val Glu Glu Ile Ile Asp Asp Val Lys Thr Tyr Leu Pro Phe
    50                  55                  60

Ile Asn Ala Ser Asn Gly Gly Ile Thr Val Ser Gly Gly Glu Pro Leu
65                  70                  75                  80

Leu Gln Ile Asp Phe Leu Ile Glu Leu Phe Lys Ala Cys Lys Lys Leu
                85                  90                  95

Gly Ile His Thr Ala Ile Asp Ser Ser Gly Gly Cys Tyr Thr Thr Glu
            100                 105                 110

Ala Ser Phe Gln Gln Lys Leu Asn Glu Leu Leu Ser Tyr Thr Asp Leu
        115                 120                 125

Ile Leu Leu Asp Leu Lys His Ile Asp Glu Lys Lys His Arg Lys Leu
    130                 135                 140

Thr Gly Lys Thr Asn Lys His Ile Leu Gln Phe Ala Gln Phe Leu Ser
145                 150                 155                 160

Glu Lys Asn Val Pro Val Trp Ile Arg His Val Leu Val Pro Thr Ile
                165                 170                 175

Thr Asp Asp Pro Asn Asp Leu Arg Arg Leu Ala Ala Phe Ile Arg Thr
```

```
                    180                 185                 190
Leu Lys Asn Val Lys Ile Glu Ile Leu Pro Tyr His Lys Leu Gly
                195                 200                 205

Val Tyr Lys Trp Lys Ala Leu Gly Leu Lys Tyr Pro Leu Glu Gly Ile
            210                 215                 220

Glu Pro Pro Ser Glu Glu Ser Val Gln Met Ala Gln Arg Ile Leu Asn
225                 230                 235                 240

Gly Thr Glu Asp Thr Val Ser Leu Ala
                245

<210> SEQ ID NO 29
<211> LENGTH: 2604
<212> TYPE: DNA
<213> ORGANISM: Geobacillus thermoglucosidans
<220> FEATURE:
<221> NAME/KEY: CDS
<222> LOCATION: (1)..(2604)

<400> SEQUENCE: 29 atg gct gtg gag gag aga gtc gtc gat aaa aaa atc gaa gta gca aaa        48
Met Ala Val Glu Glu Arg Val Val Asp Lys Lys Ile Glu Val Ala Lys
1               5                  10                  15 atg att gat gag ctt gtc gct aat gca cag aaa gcg ttg gaa caa att        96
Met Ile Asp Glu Leu Val Ala Asn Ala Gln Lys Ala Leu Glu Gln Ile
                20                  25                  30 cgc gct tac gat caa gaa acg atc gat cat atc gtg aaa gaa atg gcg       144
Arg Ala Tyr Asp Gln Glu Thr Ile Asp His Ile Val Lys Glu Met Ala
            35                  40                  45 tta gcc ggg ctc gac aag cat atg gca tta gcc aag ctt gca gta gaa       192
Leu Ala Gly Leu Asp Lys His Met Ala Leu Ala Lys Leu Ala Val Glu
        50                  55                  60 gaa aca aaa cgc ggt gta tat gaa gat aaa atc ata aaa aac ctt ttt       240
Glu Thr Lys Arg Gly Val Tyr Glu Asp Lys Ile Ile Lys Asn Leu Phe
65                  70                  75                  80 gcg aca gaa tat ata tac cac aat att aag tat gat aaa aca gtc ggg       288
Ala Thr Glu Tyr Ile Tyr His Asn Ile Lys Tyr Asp Lys Thr Val Gly
                85                  90                  95 att att cat gaa aat ccg cat gaa gaa att atc gaa att gct gag cct       336
Ile Ile His Glu Asn Pro His Glu Glu Ile Ile Glu Ile Ala Glu Pro
            100                 105                 110 gtt ggt gtt att gct ggg att acg cca gtg aca aac ccg aca tcg aca       384
Val Gly Val Ile Ala Gly Ile Thr Pro Val Thr Asn Pro Thr Ser Thr
        115                 120                 125 acg atg ttt aaa gcg tta atc tcg ata aaa aca cgc aac ccg att att       432
Thr Met Phe Lys Ala Leu Ile Ser Ile Lys Thr Arg Asn Pro Ile Ile
    130                 135                 140 ttc gct ttc cat cca tcg gcg caa cga tgc agc agc gaa gcg gca aga       480
Phe Ala Phe His Pro Ser Ala Gln Arg Cys Ser Ser Glu Ala Ala Arg
145                 150                 155                 160 gtg ctg cgc gat gcg gcg gtc cgg gca ggg gct cca gaa cat tgc att       528
Val Leu Arg Asp Ala Ala Val Arg Ala Gly Ala Pro Glu His Cys Ile
                165                 170                 175 caa tgg att gaa act cct tcg ctt gat gca acc aat cag ctt atg cac       576
Gln Trp Ile Glu Thr Pro Ser Leu Asp Ala Thr Asn Gln Leu Met His
            180                 185                 190 cat cct ggc gtt tct ctc att ttg gca act ggt ggc gcc ggc atg gtg       624
His Pro Gly Val Ser Leu Ile Leu Ala Thr Gly Gly Ala Gly Met Val
        195                 200                 205 aaa gca gcg tac agc tct gga aaa cca gct ttg ggc gtc gga cct ggc       672
Lys Ala Ala Tyr Ser Ser Gly Lys Pro Ala Leu Gly Val Gly Pro Gly
```

```
                210                 215                 220
aat gtg cct tgc tat att gaa aaa acg gca aac ata aaa cgg gcg gta      720
Asn Val Pro Cys Tyr Ile Glu Lys Thr Ala Asn Ile Lys Arg Ala Val
225                 230                 235                 240 aat gac tta att tta tcg aaa acg ttt gat aac ggc atg att tgc gct      768
Asn Asp Leu Ile Leu Ser Lys Thr Phe Asp Asn Gly Met Ile Cys Ala
                245                 250                 255 tct gaa caa gca gtc att att gat aaa gaa att tat gaa caa gta aag      816
Ser Glu Gln Ala Val Ile Ile Asp Lys Glu Ile Tyr Glu Gln Val Lys
            260                 265                 270 aaa gaa atg ata gaa aac cat tgt tat ttc tta aat gaa gaa gaa aag      864
Lys Glu Met Ile Glu Asn His Cys Tyr Phe Leu Asn Glu Glu Glu Lys
        275                 280                 285 aaa aaa gta gaa aaa ctc gtt atc aat gaa aat aca tgc gcc gtc aac      912
Lys Lys Val Glu Lys Leu Val Ile Asn Glu Asn Thr Cys Ala Val Asn
290                 295                 300 ccg gat atc gtc gga aag cca gct tat gaa att gcg aaa atg gcc ggc      960
Pro Asp Ile Val Gly Lys Pro Ala Tyr Glu Ile Ala Lys Met Ala Gly
305                 310                 315                 320 atc gct gtg ccg gaa gac aca aaa att ctt gtt gct gag tta aaa ggg     1008
Ile Ala Val Pro Glu Asp Thr Lys Ile Leu Val Ala Glu Leu Lys Gly
                325                 330                 335 gtc ggg cca aaa tat ccg ttg tct cgg gaa aaa tta agc cct gtc ctt     1056
Val Gly Pro Lys Tyr Pro Leu Ser Arg Glu Lys Leu Ser Pro Val Leu
            340                 345                 350 gct tgc tat aaa gtt aac agc acg gaa gaa gga ttt aag cgc tgt gaa     1104
Ala Cys Tyr Lys Val Asn Ser Thr Glu Glu Gly Phe Lys Arg Cys Glu
        355                 360                 365 gaa atg ctg gaa ttt ggc ggc ttg gga cat tcg gct gtc atc cat tcc     1152
Glu Met Leu Glu Phe Gly Gly Leu Gly His Ser Ala Val Ile His Ser
    370                 375                 380 gat aat caa aac gtg gtt acc gaa ttt ggc aaa cgg atg aaa gcg gga     1200
Asp Asn Gln Asn Val Val Thr Glu Phe Gly Lys Arg Met Lys Ala Gly
385                 390                 395                 400 cgg att atc gtt aat gcg cca tct tcg caa gga gca atc ggc gat att     1248
Arg Ile Ile Val Asn Ala Pro Ser Ser Gln Gly Ala Ile Gly Asp Ile
                405                 410                 415 tac aat gcg tac att ccg tca tta acg ctg gga tgc ggc aca ttt ggc     1296
Tyr Asn Ala Tyr Ile Pro Ser Leu Thr Leu Gly Cys Gly Thr Phe Gly
            420                 425                 430 gga aac tct gtt tcg aca aac gtc agt gcg att cat ctt atc aat ata     1344
Gly Asn Ser Val Ser Thr Asn Val Ser Ala Ile His Leu Ile Asn Ile
        435                 440                 445 aaa aga atg gca aaa agg acg gta aat atg caa tgg ttt aaa gtg ccg     1392
Lys Arg Met Ala Lys Arg Thr Val Asn Met Gln Trp Phe Lys Val Pro
    450                 455                 460 ccg aaa att tat ttc gaa aaa aat gct gta caa tac tta gcg aaa atg     1440
Pro Lys Ile Tyr Phe Glu Lys Asn Ala Val Gln Tyr Leu Ala Lys Met
465                 470                 475                 480 ccg gat att tcc aga gct ttt atc gtc acc gac ccg gga atg gtc aag     1488
Pro Asp Ile Ser Arg Ala Phe Ile Val Thr Asp Pro Gly Met Val Lys
                485                 490                 495 ctc gga tat gtc gat aaa gtg ctg tat tac ttg cgc aga cgc ccg gat     1536
Leu Gly Tyr Val Asp Lys Val Leu Tyr Tyr Leu Arg Arg Arg Pro Asp
            500                 505                 510 tat gtg cat agt gaa att ttc tcc gaa gta gag cca gat cct tca att     1584
Tyr Val His Ser Glu Ile Phe Ser Glu Val Glu Pro Asp Pro Ser Ile
        515                 520                 525 gag acg gta atg aaa ggt gtc gat atg atg aga agt ttc gag ccg gat     1632
```

-continued

| | | | | | | | | | | | | | | | |
|---|---|---|---|---|---|---|---|---|---|---|---|---|---|---|---|
| Glu | Thr | Val | Met | Lys | Gly | Val | Asp | Met | Met | Arg | Ser | Phe | Glu | Pro | Asp |
| | 530 | | | | 535 | | | | | 540 | | | | | |

| | | | | | | | | | | | | | | | | |
|---|---|---|---|---|---|---|---|---|---|---|---|---|---|---|---|---|
| gtg | att | atc | gcg | ctt | gga | ggc | ggc | tcg | cca | atg | gat | gcg | gca | aaa | gcg | 1680 |
| Val | Ile | Ile | Ala | Leu | Gly | Gly | Gly | Ser | Pro | Met | Asp | Ala | Ala | Lys | Ala | |
| 545 | | | | | 550 | | | | | 555 | | | | | 560 | |

| atg | tgg | ctc | ttt | tac | gag | cat | ccg | aca | gcg | gat | ttc | aac | gca | tta | aaa | 1728 |
|---|---|---|---|---|---|---|---|---|---|---|---|---|---|---|---|---|
| Met | Trp | Leu | Phe | Tyr | Glu | His | Pro | Thr | Ala | Asp | Phe | Asn | Ala | Leu | Lys | |
| | | | | | 565 | | | | | 570 | | | | | 575 | |

| caa | aaa | ttt | tta | gat | att | cga | aaa | cgc | gtt | tat | aaa | tat | cca | aaa | ctg | 1776 |
|---|---|---|---|---|---|---|---|---|---|---|---|---|---|---|---|---|
| Gln | Lys | Phe | Leu | Asp | Ile | Arg | Lys | Arg | Val | Tyr | Lys | Tyr | Pro | Lys | Leu | |
| | | | 580 | | | | | 585 | | | | | 590 | | | |

| ggc | caa | aaa | gcg | aaa | ttt | gtc | gcc | att | ccg | acg | aca | tca | gga | aca | gga | 1824 |
|---|---|---|---|---|---|---|---|---|---|---|---|---|---|---|---|---|
| Gly | Gln | Lys | Ala | Lys | Phe | Val | Ala | Ile | Pro | Thr | Thr | Ser | Gly | Thr | Gly | |
| | 595 | | | | | 600 | | | | | 605 | | | | | |

| tcg | gaa | gta | acg | tcc | ttt | gcc | gtc | att | acc | gat | aaa | aaa | acg | aat | ata | 1872 |
|---|---|---|---|---|---|---|---|---|---|---|---|---|---|---|---|---|
| Ser | Glu | Val | Thr | Ser | Phe | Ala | Val | Ile | Thr | Asp | Lys | Lys | Thr | Asn | Ile | |
| | 610 | | | | | 615 | | | | | 620 | | | | | |

| aaa | tat | ccg | ttg | gca | gat | tat | gaa | ttg | aca | ccg | gac | gtc | gcg | att | gtg | 1920 |
|---|---|---|---|---|---|---|---|---|---|---|---|---|---|---|---|---|
| Lys | Tyr | Pro | Leu | Ala | Asp | Tyr | Glu | Leu | Thr | Pro | Asp | Val | Ala | Ile | Val | |
| 625 | | | | | 630 | | | | | 635 | | | | | 640 | |

| gat | ccg | caa | ttt | gtc | atg | acc | gtg | cca | aaa | cat | gtc | acc | gcc | gat | acg | 1968 |
|---|---|---|---|---|---|---|---|---|---|---|---|---|---|---|---|---|
| Asp | Pro | Gln | Phe | Val | Met | Thr | Val | Pro | Lys | His | Val | Thr | Ala | Asp | Thr | |
| | | | | 645 | | | | | 650 | | | | | 655 | | |

| gga | atg | gat | gta | ttg | aca | cat | gcg | atc | gaa | gcg | tat | gtc | tcc | aat | atg | 2016 |
|---|---|---|---|---|---|---|---|---|---|---|---|---|---|---|---|---|
| Gly | Met | Asp | Val | Leu | Thr | His | Ala | Ile | Glu | Ala | Tyr | Val | Ser | Asn | Met | |
| | | | | 660 | | | | | 665 | | | | | 670 | | |

| gca | aat | gat | tat | acc | gat | ggt | ctt | gcc | atg | aaa | gca | atc | caa | ctc | gta | 2064 |
|---|---|---|---|---|---|---|---|---|---|---|---|---|---|---|---|---|
| Ala | Asn | Asp | Tyr | Thr | Asp | Gly | Leu | Ala | Met | Lys | Ala | Ile | Gln | Leu | Val | |
| | | | 675 | | | | | 680 | | | | | 685 | | | |

| ttt | gaa | tat | ttg | ccg | cgg | gca | tat | caa | aac | gga | gcg | gat | gag | ctt | gcc | 2112 |
|---|---|---|---|---|---|---|---|---|---|---|---|---|---|---|---|---|
| Phe | Glu | Tyr | Leu | Pro | Arg | Ala | Tyr | Gln | Asn | Gly | Ala | Asp | Glu | Leu | Ala | |
| 690 | | | | | 695 | | | | | 700 | | | | | | |

| cgg | gag | aaa | atg | cat | aac | gcc | tct | acg | att | gcg | gga | atg | gca | ttt | gcc | 2160 |
|---|---|---|---|---|---|---|---|---|---|---|---|---|---|---|---|---|
| Arg | Glu | Lys | Met | His | Asn | Ala | Ser | Thr | Ile | Ala | Gly | Met | Ala | Phe | Ala | |
| 705 | | | | | 710 | | | | | 715 | | | | | 720 | |

| aac | gcg | ttt | tta | ggc | att | aac | cat | agt | ttg | gct | cat | aaa | ctt | ggc | gcg | 2208 |
|---|---|---|---|---|---|---|---|---|---|---|---|---|---|---|---|---|
| Asn | Ala | Phe | Leu | Gly | Ile | Asn | His | Ser | Leu | Ala | His | Lys | Leu | Gly | Ala | |
| | | | | 725 | | | | | 730 | | | | | 735 | | |

| gaa | ttc | cat | att | ccg | cat | ggg | cgc | gcg | aat | acc | att | ttg | atg | ccg | cat | 2256 |
|---|---|---|---|---|---|---|---|---|---|---|---|---|---|---|---|---|
| Glu | Phe | His | Ile | Pro | His | Gly | Arg | Ala | Asn | Thr | Ile | Leu | Met | Pro | His | |
| | | | 740 | | | | | 745 | | | | | 750 | | | |

| gtc | att | cgc | tat | aac | gca | gcg | aaa | ccg | aaa | aaa | ttt | acc | gca | ttt | ccg | 2304 |
|---|---|---|---|---|---|---|---|---|---|---|---|---|---|---|---|---|
| Val | Ile | Arg | Tyr | Asn | Ala | Ala | Lys | Pro | Lys | Lys | Phe | Thr | Ala | Phe | Pro | |
| | 755 | | | | | 760 | | | | | 765 | | | | | |

| aaa | tac | gaa | tat | ttc | aaa | gcg | gac | cag | cgc | tat | gca | gaa | att | gcg | aga | 2352 |
|---|---|---|---|---|---|---|---|---|---|---|---|---|---|---|---|---|
| Lys | Tyr | Glu | Tyr | Phe | Lys | Ala | Asp | Gln | Arg | Tyr | Ala | Glu | Ile | Ala | Arg | |
| | 770 | | | | | 775 | | | | | 780 | | | | | |

| atg | ctc | ggc | ttg | ccg | gcc | cgc | aca | acg | gaa | gaa | ggg | gtc | gaa | agc | ctc | 2400 |
|---|---|---|---|---|---|---|---|---|---|---|---|---|---|---|---|---|
| Met | Leu | Gly | Leu | Pro | Ala | Arg | Thr | Thr | Glu | Glu | Gly | Val | Glu | Ser | Leu | |
| 785 | | | | | 790 | | | | | 795 | | | | | 800 | |

| gtt | cag | gcg | atc | att | aag | ctg | gca | aaa | cag | ttg | gat | atg | ccg | ctg | agc | 2448 |
|---|---|---|---|---|---|---|---|---|---|---|---|---|---|---|---|---|
| Val | Gln | Ala | Ile | Ile | Lys | Leu | Ala | Lys | Gln | Leu | Asp | Met | Pro | Leu | Ser | |
| | | | | 805 | | | | | 810 | | | | | 815 | | |

| att | gaa | gca | tgc | ggc | gtc | agc | aaa | caa | gaa | ttt | gaa | agc | aaa | gtt | gaa | 2496 |
|---|---|---|---|---|---|---|---|---|---|---|---|---|---|---|---|---|
| Ile | Glu | Ala | Cys | Gly | Val | Ser | Lys | Gln | Glu | Phe | Glu | Ser | Lys | Val | Glu | |
| | | | 820 | | | | | 825 | | | | | 830 | | | |

| aaa | tta | gcc | gaa | ttg | gct | ttc | gaa | gac | caa | tgt | act | act | gct | aac | ccg | 2544 |
|---|---|---|---|---|---|---|---|---|---|---|---|---|---|---|---|---|
| Lys | Leu | Ala | Glu | Leu | Ala | Phe | Glu | Asp | Gln | Cys | Thr | Thr | Ala | Asn | Pro | |
| | | 835 | | | | | 840 | | | | | 845 | | | | |

```
aaa ctc ccg ctt gtt agc gat tta gtt cat att tat cgc caa gcg ttt    2592
Lys Leu Pro Leu Val Ser Asp Leu Val His Ile Tyr Arg Gln Ala Phe
    850             855                 860 aaa gga gtt taa                                                    2604
Lys Gly Val
865
```

<210> SEQ ID NO 30
<211> LENGTH: 867
<212> TYPE: PRT
<213> ORGANISM: Geobacillus thermoglucosidans

<400> SEQUENCE: 30

```
Met Ala Val Glu Glu Arg Val Val Asp Lys Lys Ile Glu Val Ala Lys
1               5                   10                  15

Met Ile Asp Glu Leu Val Ala Asn Ala Gln Lys Ala Leu Glu Gln Ile
            20                  25                  30

Arg Ala Tyr Asp Gln Glu Thr Ile Asp His Ile Val Lys Glu Met Ala
        35                  40                  45

Leu Ala Gly Leu Asp Lys His Met Ala Leu Ala Lys Leu Ala Val Glu
    50                  55                  60

Glu Thr Lys Arg Gly Val Tyr Glu Asp Lys Ile Ile Lys Asn Leu Phe
65                  70                  75                  80

Ala Thr Glu Tyr Ile Tyr His Asn Ile Lys Tyr Asp Lys Thr Val Gly
                85                  90                  95

Ile Ile His Glu Asn Pro His Glu Glu Ile Ile Glu Ile Ala Glu Pro
            100                 105                 110

Val Gly Val Ile Ala Gly Ile Thr Pro Val Thr Asn Pro Thr Ser Thr
        115                 120                 125

Thr Met Phe Lys Ala Leu Ile Ser Ile Lys Thr Arg Asn Pro Ile Ile
    130                 135                 140

Phe Ala Phe His Pro Ser Ala Gln Arg Cys Ser Ser Glu Ala Ala Arg
145                 150                 155                 160

Val Leu Arg Asp Ala Ala Val Arg Ala Gly Ala Pro Glu His Cys Ile
                165                 170                 175

Gln Trp Ile Glu Thr Pro Ser Leu Asp Ala Thr Asn Gln Leu Met His
            180                 185                 190

His Pro Gly Val Ser Leu Ile Leu Ala Thr Gly Gly Ala Gly Met Val
        195                 200                 205

Lys Ala Ala Tyr Ser Ser Gly Lys Pro Ala Leu Gly Val Gly Pro Gly
    210                 215                 220

Asn Val Pro Cys Tyr Ile Glu Lys Thr Ala Asn Ile Lys Arg Ala Val
225                 230                 235                 240

Asn Asp Leu Ile Leu Ser Lys Thr Phe Asp Asn Gly Met Ile Cys Ala
                245                 250                 255

Ser Glu Gln Ala Val Ile Ile Asp Lys Glu Ile Tyr Glu Gln Val Lys
            260                 265                 270

Lys Glu Met Ile Glu Asn His Cys Tyr Phe Leu Asn Glu Glu Lys
    275                 280                 285

Lys Lys Val Glu Lys Leu Val Ile Asn Glu Asn Thr Cys Ala Val Asn
    290                 295                 300

Pro Asp Ile Val Gly Lys Pro Ala Tyr Glu Ile Ala Lys Met Ala Gly
305                 310                 315                 320

Ile Ala Val Pro Glu Asp Thr Lys Ile Leu Val Ala Glu Leu Lys Gly
                325                 330                 335
```

```
Val Gly Pro Lys Tyr Pro Leu Ser Arg Glu Lys Leu Ser Pro Val Leu
            340                 345                 350

Ala Cys Tyr Lys Val Asn Ser Thr Glu Glu Gly Phe Lys Arg Cys Glu
            355                 360                 365

Glu Met Leu Glu Phe Gly Gly Leu Gly His Ser Ala Val Ile His Ser
        370                 375                 380

Asp Asn Gln Asn Val Val Thr Glu Phe Gly Lys Arg Met Lys Ala Gly
385                 390                 395                 400

Arg Ile Ile Val Asn Ala Pro Ser Ser Gln Gly Ala Ile Gly Asp Ile
                405                 410                 415

Tyr Asn Ala Tyr Ile Pro Ser Leu Thr Leu Gly Cys Gly Thr Phe Gly
            420                 425                 430

Gly Asn Ser Val Ser Thr Asn Val Ser Ala Ile His Leu Ile Asn Ile
        435                 440                 445

Lys Arg Met Ala Lys Arg Thr Val Asn Met Gln Trp Phe Lys Val Pro
    450                 455                 460

Pro Lys Ile Tyr Phe Glu Lys Asn Ala Val Gln Tyr Leu Ala Lys Met
465                 470                 475                 480

Pro Asp Ile Ser Arg Ala Phe Ile Val Thr Asp Pro Gly Met Val Lys
                485                 490                 495

Leu Gly Tyr Val Asp Lys Val Leu Tyr Tyr Leu Arg Arg Arg Pro Asp
            500                 505                 510

Tyr Val His Ser Glu Ile Phe Ser Glu Val Glu Pro Asp Pro Ser Ile
        515                 520                 525

Glu Thr Val Met Lys Gly Val Asp Met Met Arg Ser Phe Glu Pro Asp
    530                 535                 540

Val Ile Ile Ala Leu Gly Gly Gly Ser Pro Met Asp Ala Ala Lys Ala
545                 550                 555                 560

Met Trp Leu Phe Tyr Glu His Pro Thr Ala Asp Phe Asn Ala Leu Lys
                565                 570                 575

Gln Lys Phe Leu Asp Ile Arg Lys Arg Val Tyr Lys Tyr Pro Lys Leu
            580                 585                 590

Gly Gln Lys Ala Lys Phe Val Ala Ile Pro Thr Thr Ser Gly Thr Gly
        595                 600                 605

Ser Glu Val Thr Ser Phe Ala Val Ile Thr Asp Lys Lys Thr Asn Ile
    610                 615                 620

Lys Tyr Pro Leu Ala Asp Tyr Glu Leu Thr Pro Asp Val Ala Ile Val
625                 630                 635                 640

Asp Pro Gln Phe Val Met Thr Val Pro Lys His Val Thr Ala Asp Thr
                645                 650                 655

Gly Met Asp Val Leu Thr His Ala Ile Glu Ala Tyr Val Ser Asn Met
            660                 665                 670

Ala Asn Asp Tyr Thr Asp Gly Leu Ala Met Lys Ala Ile Gln Leu Val
        675                 680                 685

Phe Glu Tyr Leu Pro Arg Ala Tyr Gln Asn Gly Ala Asp Glu Leu Ala
    690                 695                 700

Arg Glu Lys Met His Asn Ala Ser Thr Ile Ala Gly Met Ala Phe Ala
705                 710                 715                 720

Asn Ala Phe Leu Gly Ile Asn His Ser Leu Ala His Lys Leu Gly Ala
                725                 730                 735

Glu Phe His Ile Pro His Gly Arg Ala Asn Thr Ile Leu Met Pro His
            740                 745                 750

Val Ile Arg Tyr Asn Ala Ala Lys Pro Lys Lys Phe Thr Ala Phe Pro
```

```
                755                 760                 765
Lys Tyr Glu Tyr Phe Lys Ala Asp Gln Arg Tyr Ala Glu Ile Ala Arg
        770                 775                 780

Met Leu Gly Leu Pro Ala Arg Thr Thr Glu Glu Gly Val Glu Ser Leu
785                 790                 795                 800

Val Gln Ala Ile Ile Lys Leu Ala Lys Gln Leu Asp Met Pro Leu Ser
            805                 810                 815

Ile Glu Ala Cys Gly Val Ser Lys Gln Glu Phe Glu Ser Lys Val Glu
                820                 825                 830

Lys Leu Ala Glu Leu Ala Phe Glu Asp Gln Cys Thr Thr Ala Asn Pro
        835                 840                 845

Lys Leu Pro Leu Val Ser Asp Leu Val His Ile Tyr Arg Gln Ala Phe
    850                 855                 860

Lys Gly Val
865

<210> SEQ ID NO 31
<211> LENGTH: 975
<212> TYPE: DNA
<213> ORGANISM: Geobacillus thermoglucosidans
<220> FEATURE:
<221> NAME/KEY: CDS
<222> LOCATION: (1)..(975)

<400> SEQUENCE: 31 gtg agc agt gat tta ttt tcg aca tta aaa gaa aaa ata gcg gga aaa        48
Val Ser Ser Asp Leu Phe Ser Thr Leu Lys Glu Lys Ile Ala Gly Lys
1               5                   10                  15 caa cgg aaa atc gtg ttt ccg gaa ggg ctt gat gag cgt att tta aca        96
Gln Arg Lys Ile Val Phe Pro Glu Gly Leu Asp Glu Arg Ile Leu Thr
            20                  25                  30 gcg gta agc cgt ctg gcg aac gag caa atc gtc acg ccg att gtc att       144
Ala Val Ser Arg Leu Ala Asn Glu Gln Ile Val Thr Pro Ile Val Ile
        35                  40                  45 ggc aat gaa gaa gcg gtt aag caa aaa gca agc gag ctt ggg ctg acg       192
Gly Asn Glu Glu Ala Val Lys Gln Lys Ala Ser Glu Leu Gly Leu Thr
    50                  55                  60 ctt ccg aat gtc gaa atc att gat ccg cat cag tac ggg gaa atg gac       240
Leu Pro Asn Val Glu Ile Ile Asp Pro His Gln Tyr Gly Glu Met Asp
65                  70                  75                  80 aag ctt gtt gcg gca ttt gtc gaa cgc cgc aaa ggg aaa gtg acg gaa       288
Lys Leu Val Ala Ala Phe Val Glu Arg Arg Lys Gly Lys Val Thr Glu
                85                  90                  95 gaa gcg gcg cgg aag ctg ctt ctt gac gaa aat tat ttt ggc acc atg       336
Glu Ala Ala Arg Lys Leu Leu Leu Asp Glu Asn Tyr Phe Gly Thr Met
            100                 105                 110 ctt gtg tac atg gat aag gcg cat ggg ctt gtc agc ggc gcg gcg cat       384
Leu Val Tyr Met Asp Lys Ala His Gly Leu Val Ser Gly Ala Ala His
        115                 120                 125 tcg acg gct gat acg gtg cgg cct gcg ttg caa att ata aaa acg aaa       432
Ser Thr Ala Asp Thr Val Arg Pro Ala Leu Gln Ile Ile Lys Thr Lys
    130                 135                 140 caa ggc gtc cgc aaa acg tca gga gta ttc att atg gtg cgc ggt gat       480
Gln Gly Val Arg Lys Thr Ser Gly Val Phe Ile Met Val Arg Gly Asp
145                 150                 155                 160 gaa aag tac gtg ttt gcc gat tgc gcg atc aac att gcc ccg gac agc       528
Glu Lys Tyr Val Phe Ala Asp Cys Ala Ile Asn Ile Ala Pro Asp Ser
                165                 170                 175 caa gat ttg gcg gaa atc gct gtc gaa agc gcc aac acg gca aaa atg       576
Gln Asp Leu Ala Glu Ile Ala Val Glu Ser Ala Asn Thr Ala Lys Met
```

```
Gln Asp Leu Ala Glu Ile Ala Val Glu Ser Ala Asn Thr Ala Lys Met
            180                 185                 190 ttc gac att gag ccg cgc gtg gcg atg ttg agc ttt tcg aca aaa gga        624
Phe Asp Ile Glu Pro Arg Val Ala Met Leu Ser Phe Ser Thr Lys Gly
            195                 200                 205 tca gcg aaa tcg cca gaa acg gaa aaa gtc gtc gaa gcg gtg cgg ctt        672
Ser Ala Lys Ser Pro Glu Thr Glu Lys Val Val Glu Ala Val Arg Leu
210                 215                 220 gcg aaa gaa atg gcg cct gac tta gtg ctg gac ggt gag ttt cag ttc        720
Ala Lys Glu Met Ala Pro Asp Leu Val Leu Asp Gly Glu Phe Gln Phe
225                 230                 235                 240 gac gcg gcg ttt gtt ccg tct gtc gcg aaa aag aaa gcg cca gat tcc        768
Asp Ala Ala Phe Val Pro Ser Val Ala Lys Lys Lys Ala Pro Asp Ser
            245                 250                 255 gtc att caa gga gac gcg aac gta ttt att ttc cca agc ctt gaa gcg        816
Val Ile Gln Gly Asp Ala Asn Val Phe Ile Phe Pro Ser Leu Glu Ala
            260                 265                 270 gga aat atc ggc tat aaa atc gcc cag cgt ctc ggc aac ttt gaa gcg        864
Gly Asn Ile Gly Tyr Lys Ile Ala Gln Arg Leu Gly Asn Phe Glu Ala
            275                 280                 285 gtc ggc ccg att ttg caa gga ctc aat aag cct gtg aac gac ctg tca        912
Val Gly Pro Ile Leu Gln Gly Leu Asn Lys Pro Val Asn Asp Leu Ser
290                 295                 300 cgc ggt tgc aat gcg gaa gat gtg tac aag ctg acg ctt ata act gcg        960
Arg Gly Cys Asn Ala Glu Asp Val Tyr Lys Leu Thr Leu Ile Thr Ala
305                 310                 315                 320 gcg caa tcg cta taa                                                    975
Ala Gln Ser Leu <210> SEQ ID NO 32
<211> LENGTH: 324
<212> TYPE: PRT
<213> ORGANISM: Geobacillus thermoglucosidans

<400> SEQUENCE: 32

Val Ser Ser Asp Leu Phe Ser Thr Leu Lys Glu Lys Ile Ala Gly Lys
1               5                   10                  15

Gln Arg Lys Ile Val Phe Pro Glu Gly Leu Asp Glu Arg Ile Leu Thr
            20                  25                  30

Ala Val Ser Arg Leu Ala Asn Glu Gln Ile Val Thr Pro Ile Val Ile
        35                  40                  45

Gly Asn Glu Glu Ala Val Lys Gln Lys Ala Ser Glu Leu Gly Leu Thr
    50                  55                  60

Leu Pro Asn Val Glu Ile Ile Asp Pro His Gln Tyr Gly Glu Met Asp
65                  70                  75                  80

Lys Leu Val Ala Ala Phe Val Glu Arg Arg Lys Gly Lys Val Thr Glu
                85                  90                  95

Glu Ala Ala Arg Lys Leu Leu Leu Asp Glu Asn Tyr Phe Gly Thr Met
            100                 105                 110

Leu Val Tyr Met Asp Lys Ala His Gly Leu Val Ser Gly Ala Ala His
        115                 120                 125

Ser Thr Ala Asp Thr Val Arg Pro Ala Leu Gln Ile Ile Lys Thr Lys
    130                 135                 140

Gln Gly Val Arg Lys Thr Ser Gly Val Phe Ile Met Val Arg Gly Asp
145                 150                 155                 160

Glu Lys Tyr Val Phe Ala Asp Cys Ala Ile Asn Ile Ala Pro Asp Ser
                165                 170                 175
```

```
Gln Asp Leu Ala Glu Ile Ala Val Glu Ser Ala Asn Thr Ala Lys Met
        180                 185                 190

Phe Asp Ile Glu Pro Arg Val Ala Met Leu Ser Phe Ser Thr Lys Gly
            195                 200                 205

Ser Ala Lys Ser Pro Glu Thr Glu Lys Val Val Glu Ala Val Arg Leu
        210                 215                 220

Ala Lys Glu Met Ala Pro Asp Leu Val Leu Asp Gly Glu Phe Gln Phe
225                 230                 235                 240

Asp Ala Ala Phe Val Pro Ser Val Ala Lys Lys Ala Pro Asp Ser
            245                 250                 255

Val Ile Gln Gly Asp Ala Asn Val Phe Ile Phe Pro Ser Leu Glu Ala
        260                 265                 270

Gly Asn Ile Gly Tyr Lys Ile Ala Gln Arg Leu Gly Asn Phe Glu Ala
        275                 280                 285

Val Gly Pro Ile Leu Gln Gly Leu Asn Lys Pro Val Asn Asp Leu Ser
        290                 295                 300

Arg Gly Cys Asn Ala Glu Asp Val Tyr Lys Leu Thr Leu Ile Thr Ala
305                 310                 315                 320

Ala Gln Ser Leu

<210> SEQ ID NO 33
<211> LENGTH: 750
<212> TYPE: DNA
<213> ORGANISM: Geobacillus thermoglucosidans
<220> FEATURE:
<221> NAME/KEY: CDS
<222> LOCATION: (1)..(750)

<400> SEQUENCE: 33 atg gat gtc gat gtc aag cga gat cag acg ctg tta aaa gat cat gag      48
Met Asp Val Asp Val Lys Arg Asp Gln Thr Leu Leu Lys Asp His Glu
1               5                   10                  15 atg aaa aag ctt att cgc cgc agc caa gag ggg gac caa cag gcg cgc      96
Met Lys Lys Leu Ile Arg Arg Ser Gln Glu Gly Asp Gln Gln Ala Arg
            20                  25                  30 aat gaa att atc caa aaa aac atg cgc ctc gtt tgg tcg gtc gtc cag     144
Asn Glu Ile Ile Gln Lys Asn Met Arg Leu Val Trp Ser Val Val Gln
        35                  40                  45 cgc ttt ttg aac cgc gga tac gag ccg gac gat tta ttt caa att ggc     192
Arg Phe Leu Asn Arg Gly Tyr Glu Pro Asp Asp Leu Phe Gln Ile Gly
    50                  55                  60 tgc atc ggc ttg ctt aaa tct gtt gat aag ttt gat ttg tcg tat gac     240
Cys Ile Gly Leu Leu Lys Ser Val Asp Lys Phe Asp Leu Ser Tyr Asp
65                  70                  75                  80 gtg aag ttt tcc aca tat gcg gtg ccg atg atc atc ggc gaa att cag     288
Val Lys Phe Ser Thr Tyr Ala Val Pro Met Ile Ile Gly Glu Ile Gln
                85                  90                  95 cgg ttt atc cgc gat gac ggg acg gtg aaa gtg agc cgt tcc tta aaa     336
Arg Phe Ile Arg Asp Asp Gly Thr Val Lys Val Ser Arg Ser Leu Lys
            100                 105                 110 gaa acg ggc aat aaa atc cgg aaa gca aga gac gag ctt tcg aaa aaa     384
Glu Thr Gly Asn Lys Ile Arg Lys Ala Arg Asp Glu Leu Ser Lys Lys
        115                 120                 125 cat gga cgg gcg cca acg gtg aca gaa atc gcc gat tat tta gaa att     432
His Gly Arg Ala Pro Thr Val Thr Glu Ile Ala Asp Tyr Leu Glu Ile
    130                 135                 140
```

```
tct cca gaa gaa gtg gtg ctt gcc cag gaa gcc gtt cgt tcc ccg gct      480
Ser Pro Glu Glu Val Val Leu Ala Gln Glu Ala Val Arg Ser Pro Ala
145                 150                 155                 160 tcc att cac gaa aca gtg tat gaa aac gac ggc gac ccg atc acg ctc      528
Ser Ile His Glu Thr Val Tyr Glu Asn Asp Gly Asp Pro Ile Thr Leu
                165                 170                 175 ctc gat caa att gct gat gcc gac gaa gca tca tgg ttt gat aaa atc      576
Leu Asp Gln Ile Ala Asp Ala Asp Glu Ala Ser Trp Phe Asp Lys Ile
            180                 185                 190 gcg ttg aaa aaa gcg att gag gag ctg gat gaa cgg gaa cgt ctc atc      624
Ala Leu Lys Lys Ala Ile Glu Glu Leu Asp Glu Arg Glu Arg Leu Ile
        195                 200                 205 gtc tat ttg cgt tat tac aaa gat caa acc cag tcg gaa gtg gca tca      672
Val Tyr Leu Arg Tyr Tyr Lys Asp Gln Thr Gln Ser Glu Val Ala Ser
    210                 215                 220 aga tta ggc atc tct caa gtt caa gta tcc cgt ctt gaa aaa aaa att      720
Arg Leu Gly Ile Ser Gln Val Gln Val Ser Arg Leu Glu Lys Lys Ile
225                 230                 235                 240 tta cag caa ata aag gag aga atg gat ggg                              750
Leu Gln Gln Ile Lys Glu Arg Met Asp Gly
                245                 250
```

<210> SEQ ID NO 34
<211> LENGTH: 250
<212> TYPE: PRT
<213> ORGANISM: Geobacillus thermoglucosidans

<400> SEQUENCE: 34

```
Met Asp Val Asp Val Lys Arg Asp Gln Thr Leu Leu Lys Asp His Glu
1               5                   10                  15

Met Lys Lys Leu Ile Arg Arg Ser Gln Glu Gly Asp Gln Gln Ala Arg
            20                  25                  30

Asn Glu Ile Ile Gln Lys Asn Met Arg Leu Val Trp Ser Val Val Gln
        35                  40                  45

Arg Phe Leu Asn Arg Gly Tyr Glu Pro Asp Asp Leu Phe Gln Ile Gly
    50                  55                  60

Cys Ile Gly Leu Leu Lys Ser Val Asp Lys Phe Asp Leu Ser Tyr Asp
65                  70                  75                  80

Val Lys Phe Ser Thr Tyr Ala Val Pro Met Ile Ile Gly Glu Ile Gln
            85                  90                  95

Arg Phe Ile Arg Asp Asp Gly Thr Val Lys Val Ser Arg Ser Leu Lys
        100                 105                 110

Glu Thr Gly Asn Lys Ile Arg Lys Ala Arg Asp Glu Leu Ser Lys Lys
    115                 120                 125

His Gly Arg Ala Pro Thr Val Thr Glu Ile Ala Asp Tyr Leu Glu Ile
130                 135                 140

Ser Pro Glu Glu Val Val Leu Ala Gln Glu Ala Val Arg Ser Pro Ala
145                 150                 155                 160

Ser Ile His Glu Thr Val Tyr Glu Asn Asp Gly Asp Pro Ile Thr Leu
            165                 170                 175

Leu Asp Gln Ile Ala Asp Ala Asp Glu Ala Ser Trp Phe Asp Lys Ile
        180                 185                 190

Ala Leu Lys Lys Ala Ile Glu Glu Leu Asp Glu Arg Glu Arg Leu Ile
    195                 200                 205
```

-continued

```
Val Tyr Leu Arg Tyr Tyr Lys Asp Gln Thr Gln Ser Glu Val Ala Ser
    210                 215                 220

Arg Leu Gly Ile Ser Gln Val Gln Val Ser Arg Leu Glu Lys Lys Ile
225                 230                 235                 240

Leu Gln Gln Ile Lys Glu Arg Met Asp Gly
                245                 250
```

GENETIC MODIFICATION OF (S)-LACTIC ACID PRODUCING THERMOPHILIC BACTERIA

The present invention relates to modifying a thermophilic bacterial cell for homolactic and enantiopure (S)-lactic acid production, a genetically modified cell, and a method to produce enantiomeric pure (S)-lactic acid.

Lactic acid and its salts, known as lactate, are commercially viable products useful in various fields including medicine, biodegradable polymers and food processing. Thermophilic bacteria, such as *Geobacillus*, that are facultative anaerobic seem ideal organisms for the industrial manufacture of lactic acid. They are capable of growing at temperatures between 37-75° C., with an optimum at 55-65° C. (Nazina et al., 2001, Int. J. Syst. Evol. Microbiol. 51:433-446) and allow anaerobic industrial fermentation at temperatures above 50° C. This high temperature has several advantages when fermenting on industrial scale: less risk of infections and thus higher enantiomeric purity, faster reactions, lower cooling costs, etcetera. The facultative anaerobic nature of the Geobacilli allows fermentation under anaerobic conditions, or at least under a low partial pressure of oxygen, which for Industrial scale is desirable because it allows for relatively inexpensive equipment and processing. Furthermore, the nutrient requirements of these bacteria are less demanding than those of lactic acid bacteria such as *Lactobacillus* species which also allows for relatively inexpensive industrial processes.

*Geobacillus* species that are facultative anaerobic are known to produce lactic acid when grown under anaerobic conditions, or at least under a low partial pressure of oxygen. Examples are *G. caldotenax*, *G. caldoxylosilyticus*, *G. debilis*, *G. kaustophilus*, *G. pallidus*, *G. stearothermophilus*, *G. tepidimans*, *G. thermodenitrificans*, *G. thermoglucosidans*, *G. thermoleovorans*, *G. toebii*, *G. tropicalis*.

*G. thermoglucosidans* can produce lactic acid from xylose, arabinose, glucose, fructose, sucrose and cellobiose (Green et al., 2003, WO03/008601). For industrial applications feedstocks containing sucrose, glucose, xylose, or arabinose, or mixtures thereof, are most relevant. The ability to simultaneously utilize glucose and xylose (Green et al., 2003, WO03/008601) is an important advantage of *G. thermoglucosidans* when using fermentable sugars derived from lignocellulosic feedstocks.

One disadvantage of the known *Geobacillus* species which are facultative anaerobic is the fact that they have a mixed acid fermentation, producing lactic acid, ethanol, acetic acid, and formic acid as main fermentation products. In this application the term organic acids also is meant to also include their corresponding salts.

Another disadvantage is that most species do not produce enantiomeric pure lactic acid. Chiral purity is an important aspect for production of poly-lactic acid polymers. Therefore, it is essential to produce enantiopure (S)-lactic acid for commercial applications. However, to date only limited information is available on the enantiopurity of the lactic acid produced by *Geobacillus* species. It is to be understood that other terms for (S)-lactic acid are L-lactic acid or L(+)-lactic acid. In this application these terms are interchangeably used. Similarly, the terms (R)-lactic acid, D-lactic acid and D(−)-lactic acid are interchangeably used.

Payton & Hartley show that *G. stearothermophilus* PSII has a mixed acid fermentation profile producing (S)-lactic acid, acetic acid, and ethanol when grown on glucose in non-pH-controlled shake-flask conditions (Payton & Hartley, 1985, FEMS Microbiol. Lett. 26:333-336). Chiral purity is not mentioned. Later studies show that PSII and its derivatives are atypical for *G. stearothermophilus* and seem more closely related to *G. caldotenax* (Amartey et al., 1991, Biotechnol. Lett. 13:621-626; Green et al., 2001, WO 01/49865). The low yield makes this strain not suited for industrial application.

Danner et al. show production of (S)-lactic acid by *G. stearothermophilus* IFA6 and IFA9 from sucrose and glucose (Danner et al., 1998, Appl. Biochem. Biotechnol. 70-72:895-903). Strain IFA6 produces significant amounts of ethanol, acetic acid and formic acid by-products from glucose, while strain IFA9 does not. Chiral purity was reported between 99.22 and 99.85% for IFA6 and 99.4% for IFA9, when grown on glucose (Danner et al., 1998, Appl. Biochem. Biotechnol. 70-72:895-903). Culture conditions were based on using rich medium containing yeast extract and casein peptone, which are not desirable for industrial production. Compared to strain IFA6 strain IFA9 has reduced productivity at higher product concentrations, making it less suitable for industrial production. In addition, strain IFA6 suffered from a low yield, making it also not suited for industrial production.

Rao & Satyanarayana show lactic acid production with *G. thermoleovorans*, but do not comment on the yield nor chiral purity (Rao & Satyanarayana, 2009, Appl. Biochem. Biotechnol. 159:464-477).

Green et al. disclose (S)-lactic acid production with *G. thermoglucosidans* LN-9 with a chiral purity of 99.2% and a yield of 0.7 g/g in non-pH-controlled shake-flask conditions (Green et al., 2003, WO 03/008601). The low yield makes it not suited for industrial applications.

Atkinson et al. demonstrate lactic acid production with *G. thermoglucosidans* NCIMB 11955 from xylose or glucose with significant amounts of ethanol, acetic acid and formic acid by-products (Atkinson et al., 2006, WO 2006/117536). Yield on glucose was 0.64 g/g, which is too low for industrial application. Chiral purity was not disclosed.

Tang et al. demonstrate (S)-lactic acid production with *G. thermoglucosidans* M10EXG. Under microaerobic conditions lactic acid was the main product, with acetic acid, ethanol, and formic acid as significant by-products. Under anaerobic conditions formic acid was the main product, with lactic acid, acetic acid, and ethanol as major by-products. The yields described are too low for industrial application. The chiral purity of the (S)-lactic acid was reported to be >99% (Tang et al., 2009, Biotechnol. Lett. 102: 1377-1386).

*G. thermoglucosidans* is described as a thermophilic *Bacillus* species (Suzuki et al., 1983, Syst. Appl. Microbiol. 4:487-495; Nazina et al., 2001, Int. J. Syst. Evol. Microbiol. 51:433-446; Coorevits et al., 2012, Int. Syst. Evol. Microbiol. 62:14770-1485). *G. thermoglucosidans* was previously known as *Bacillus thermoglucosidasius* (Suzuki et al., 1983, Syst. Appl. Microbiol. 4:487-495), which was renamed to *G. thermoglucosidasius* by Nazina et al. in 2001 (Nazina et al., 2001, Int. J. Syst. Evol. Microbiol. 51:433-446), and later renamed to *G. thermoglucosidans* by Coorevits et al. (Coorevits et al., 2012, Int. Syst. Evol. Microbiol. 62:14770-1485). The type strain was isolated from soil (Suzuki et al., 1976, Appl. Environ. Microbiol. 31:807-812). Although originally reported as strictly aerobic, later studies report facultative anaerobic growth and (S)-lactic acid production (Green et al., 2003, WO 03/008601; Fong et al., 2006, Extremophiles 10:363-372). Temperature range is between 42 and 69° C., with an optimum of 62° C. (Suzuki et al., 1983, Syst. Appl. Microbiol. 4:487-495). Genetic modification of *G. thermoglucosidans* strains for ethanol production has been reported (Green et al., 2001, WO 01/49865;

Atkinson et al., 2008, WO08/038019). This includes description of the genetic tools for *G. thermoglucosidans* DSM 2542$^T$ and a method to disrupt the L-lactate dehydrogenase (ldh) gene (Atkinson et al., 2006, WO2006/117536 and 2008, WO2008/038019). Metabolic pathways and fluxes for cells grown on xylose and glucose have been reported for *G. thermoglucosidans* M10EXG (Tang et al. 2009, Biotechnol. Lett. 102: 1377-1386).

In our laboratory we have observed that chiral purity of the acid produced by *G. thermoglucosidans* DSM 2542 can vary, depending on the medium composition and/or sugar source. We have seen (S)-lactic acid chiral purities between 89 and >99%. However, for flexibility in substrate choice and medium composition there is a need for a derivative that produces enantiopure (S)-lactic acid under all industrial relevant conditions.

It can be concluded from the foregoing that known *Geobacillus* strains have a mixed acid fermentation and do not show homolactic and enantiopure lactic acid production.

There is a clear need to be able to use bacterial strains (e.g. *Geobacillus* strains) for homolactic and enantiopure lactic acid production that have attractive characteristics for industrial application, such as low nutrient needs, broad sugar consumption capabilities, the capacity to produce carbohydrolytic enzymes, high growth rate, high productivity, resistance to osmotic stress, and genetic accessibility.

One of the objects of the present invention is to produce a thermophilic bacterial cell that is facultative anaerobic and produces (S)-lactic acid by homolactic fermentation.

Another object of the present invention is to produce a thermophilic bacterial cell that is facultative anaerobic and produces enantiopure (S)-lactic acid.

(S)-lactic acid yield and chiral purity in the lactic acid production with *Geobacillus* species that are facultative anaerobic may vary depending on the strain and the culture conditions. Therefore, there is a need for an improved *Geobacillus* that is modified to produce chiral pure (S)-lactic acid in a homolactic manner.

There are several options that can result in chiral impurity as described in literature. (R)-lactic acid can be formed from pyruvate by the activity of a D-lactate dehydrogenase, it can be formed from (S)-lactic acid by the activity of a lactate racemase, or it can be formed through the methylglyoxal pathway.

Methylglyoxal synthase (E.C. 4.2.99.11) catalyzes the conversion of dihydroxyacetone phosphate to methylglyoxal and orthophosphate in the first step of the methylglyoxal bypass. Next, methylglyoxal can be converted via two different pathways to (S)- or (R)-lactic acid. Therefore, the methylglyoxal bypass could be a source of chiral contamination for production of both (S)- and (R)-lactic acid. In *Escherichia coli* disruption of the mgsA gene encoding methylglyoxal synthase improved the chiral purity for production of both (S)- and (R)-lactic acid (Grabar et al., 2006, Biotechnol. Lett. 28:1527-1535). In Gram-positives little is known on the activity of the methylglyoxal pathway. In the mesophilic *Bacillus subtilis* the mgsA gene is encoded in an operon together with genes encoding the first two enzymes in bacillithiol biosynthesis (Gaballa et al., 2010, Proc. Natl. Acad. Sci. USA 107:6482-6486; Helmann, 2011, Antioxidants & Redox signaling 15:123-133). Recently, Chandrangsu et al. have demonstrated that bacillithiol is involved in methylglyoxal detoxification (Chandrangsu et al., 2014, Mol. Microbiol. 91:706-715). The bacillithiol-dependent methylglyoxal pathway utilizes glyoxalase I (GlxA) and glyoxalase II (FlxB) to convert methylglyoxal to (R)-lactic acid (Chandrangsu et al., 2014). In addition, methylglyoxal can be converted to (R)-lactic acid by the activity of YdeA, YraA, and YfkM, predicted homologues of glyoxalase III (Chandrangsu et al., 2014, Mol. Microbiol. 91:706-715).

From the genome sequence of *G. thermoglucosidans* we could retrieve a predicted D-lactate dehydrogenase gene, but no apparent lactate racemase gene. For both pathways for the conversion of methylglyoxal to (R)-lactic acid, as characterized in *B. subtilis* (Chandrangsu et al., 2014, Mol. Microbiol. 91:706-715), closest homologues in *G. thermoglucosidans* have very low amino acid sequence identity (46% for YwbC; 34% for YurT; no homologue found for YdeA; 30% for YraA; and 35% for YfkM). In contrast, the *B. subtilis* MgsA has a *G. thermoglucosidans* homologue with 72% amino acid sequence identity. Based on the genome information one would expect that the (R)-lactic acid production is caused by D-lactate dehydrogenase activity, and not by a lactate racemase or by the methylglyoxal pathway. Surprisingly, we were able to abolish (R)-lactate production by disrupting the mgsA gene, predicted to encode methylglyoxal synthase.

*Geobacillus* species that are facultative anaerobic show mixed acid fermentations with lactic acid, ethanol, acetic acid, and formic acid as main products. Disruption of genes encoding essential enzymes in production of by-products is a common approach to improve production of a desired product. However, effects of the disruption of a specific gene can have different side-effects depending on the overall metabolism of the host. Single mutations in *Escherichia coli* pflA, encoding pyruvate-formate lyase activating enzyme, and adhE, encoding bifunctional acetaldehyde-CoA/alcohol dehydrogenase complex, result in improved lactic acid production with concomitant increased pyruvate by-product formation, residual acetic acid and ethanol production and strongly reduced biomass yield (pflA$^-$) or improved lactic acid production with acetic acid as main fermentation product (adhE) (Zhu & Shimizu, 2005, Metab. Eng. 7:104-115). In several *E. coli* strains the focA-pflAB locus has been disrupted to eliminate formic acid production (Zhou et al., 2003, Appl. Environ. Microbiol. 69:2237-2244; Liu et al., 2011, Appl. Biochem. Biotechnol. 164:162-169). The importance of focA, encoding a formate channel protein, in lactic acid accumulation in the medium was recently shown (Beyer et al., 2013, J. Bacteriol. 195:1428-1435), so it will be contributing to the phenotypes of *E. coli* strains having focA-pflAB deletions. In the green alga *Chlamydomonas reinhardtii* knockouts of genes coding for pyruvate formate lyase and alcohol dehydrogenase improved lactic acid fermentation, but also increased extracellular glycerol and acetic acid concentrations (Catalanotti et al., 2012, Plant Cell 24:692-707).

In *G. thermoglucosidans* the pflBA genes are convergently oriented to the adhE gene. For practical reasons we decided to disrupt pflA, pflB, and adhE by deleting pflBA and part of adhE in one modification. Surprisingly, we were able to nearly abolish ethanol, acetic acid, and formic acid by-product formation without impacting other by-products and without impacting lactic acid fermentation performance. For instance, in the instant application that the by-product formation is nearly abolished means that by fermenting a genetically engineered cell as described herein the weight amount of by-products (such as ethanol, acetic acid, and formic acid) with respect to the total amount of lactic acid produced is of no more than 10% (w/w), and in particular no more than 5%, 4%, 3% or 2% (w/w). The amount of lactic acid and of by-products can be determined by methods known in the art, e.g. by derivatisation and analysis by gas-liquid chromatography (GLC) or High-performance liquid chromatography (HPLC).

Sporulation deficiency is a desired property for industrial application of *Bacillus* species. According to Directive 2009/41/EC of the European Parliament and of the Council of 6 May 2009 on the contained use of genetically modified micro-organisms, contained uses of genetically modified micro-organisms should be classified in relation to the risk they present to human health and the environment. Having an sporulation-deficient phenotype for *Bacillus* species is seen as a means to minimize the risk of spreading in the environment. Different methods are known to obtain sporulation-deficient phenotypes, including selecting spontaneous sporulation-deficient derivatives (Green et al., 2001, WO01/49865) or directed disruption of the sporulation pathway e.g., by disrupting spo0A (Gonzy-Treboul et al., 1992, J. Mol. Biol. 244:967-979; Atkinson et al., 2010, WO2010/052499) or sigF (Fleming et al., 1995, Appl. Environ. Microbiol. 61:3775-3780; Wang et al., 2005, J. Appl. Microbiol. 98:761-767; Kovács et al., 2010, Appl. Environ. Microbiol. 76:4085-4088).

Thus, in a first aspect, the present invention discloses a genetically engineered thermophilic bacterial cell that is facultative anaerobic and (S)-lactic acid producing comprising inactivation or deletion of the endogenous methylglyoxal synthase gene mgsA.

Endogenous genes are genes which are present in a microorganism. It goes without saying that a bacterium as described herein wherein a gene is inactivated or deleted requires for the gene to be inherently present in the bacterium. In absence of an indication to the contrary, in the present application any reference to a gene means an endogenous gene. Genes which are introduced into a microorganism are not endogenous genes.

In another aspect there is provided a genetically engineered bacterial cell that is facultative anaerobic which is homolactic and produces (S)-lactic acid in an enantiomeric pure form.

In the present invention homolactic fermentation is defined by producing lactic acid from hydrocarbon sources with the formation of no more than 15% (w/w), preferably no more than 10% (w/w), and more preferably no more than 5%, 4%, 3% or 2% (w/w) of by-products such as formic acid, acetic acid and ethanol. This percentage relates to the total weight of byproducts over the total weight of lactic acid (including (S)-lactic acid and any (R)-lactic acid that may be present). The amount of lactic acid and ethanol, acetic acid, and formic acid can be determined by methods known in the art, e.g. by derivatisation and analysis by gas-liquid chromatography (GLC) or High-performance liquid chromatography (HPLC).

In several embodiments, the formed amount of at least one of formic acid, ethanol and acetic acid is no more than 10% (w/w) based on the total weight of formic acid, ethanol or acetic acid over the total weight of lactic acid produced, in particular no more than 6%, 1%, 0.25% or 0.1% (w/w). In other words, the amount of formic acid formed in the homolactic fermentation may be, e.g., of no more than 10% (w/w) and more in particular no more than 6%, 1%, 0.25% or 0.1% (w/w) relative to the total weight amount of lactic acid. Similarly the amount of ethanol may be of no more than 10%, 6%, 1%, 0.25% or 0.1% (w/w) and the amount of acetic acid may be of no more than 10%, 6%, 1%, 0.25% or 0.1% (w/w).

In the present specification mgsA refers to the methylglyoxal synthase gene the sequence of which is provided in SEQ ID NO:23 for *Geobacillus thermoglucosidans*. The encoded amino acid sequence is provided in SEQ ID NO:24. The nucleotide regions flanking mgsA can be identified by PCR primers SEQ ID NOs 11, 12, 15 and 16.

In another aspect the invention relates to a genetically engineered thermophilic bacterial cell wherein, in addition to the mgsA gene, also the endogenous pyruvate-formate lyase A and/or B gene is inactivated or deleted.

In a preferred embodiment the pyruvate-formate lyase gene is inactivated by inactivation or deletion of the pyruvate-formate lyase/alcohol dehydrogenase locus pflBA-adhE. Alternatively, the pyruvate lyase A and/or B gene and the alcohol dehydrogenase genes adhE can be inactivated or deleted in separate steps. The nucleotide regions flanking pflBA-adhE can be identified by PCR primers SEQ ID NOs 19-21.

In the present specification with pflBA is meant the pyruvate-formate lyase genes A and B, encoding pyruvate-formate lyase activating enzyme and pyruvate formate lyase, respectively.

plfA refers to the pyruvate formate lyase A gene (encoding pyruvate-formate lyase activating enzyme) the sequence of which is provided in SEQ ID NO:27 for *Geobacillus thermoglucosidans*. The encoded amino acid sequence is provided in SEQ ID NO:28. plfB refers to the pyruvate formate lyase B gene (encoding pyruvate formate lyase) the sequence of which is provided in SEQ ID NO:25. The encoded amino acid sequence is provided in SEQ ID NO:26. In the present invention adhE refers to the alcohol dehydrogenase gene E, encoding bifunctional acetaldehyde-CoA/alcohol dehydrogenase complex, the sequence of which is provided in SEQ ID NO:29 for *Geobacillus thermoglucosidans*. The encoded amino acid sequence is provided in SEQ ID NO:30.

In yet another embodiment according to the present invention in the genetically engineered cell also the endogenous phosphotransacetylase gene (pta) is inactivated or deleted. The nucleotide sequence of pta is provided in SEQ ID NO. 31 for *Geobacillus thermoglucosidans*. The encoded amino acid sequence is provided in SEQ ID NO. 32. Inactivation or deletion of pta (which encodes phosphotransacetylase) further minimizes the remnant acetate production associated to endogenous pta activity. The resulting strain (with inactivated or deleted pta) is auxotrophic for acetic acid. Accordingly, when fermenting this genetically engineered cell acetic acid which has to be supplemented to the growth medium.

In yet another embodiment according to the present invention the genetically engineered thermophilic bacterial cell in addition is made sporulation-deficient by inactivation or deletion of an endogenous sporulation gene.

In another embodiment the inactivated or deleted sporulation gene is sigF.

sigF refers to a sporulation gene the nucleotide sequence of which is provided in SEQ ID NO: 33 for *Geobacillus thermoglucosidans*. The encoded amino acid sequence is provided in SEQ ID NO: 34. The nucleotide sequences flanking SigF can be identified by PCR primers SEQ ID NOs 3-6.

In another embodiment according to the present invention (S)-lactic acid is produced in the cell according to the invention with an enantiomeric purity of at least 98%, more preferably at least 99%, 99.5%, 99.8% or 99.9%.

In yet another embodiment of the present invention in the cell one or more of the genes mgsA, pflBA-adhE or sigF are inactivated or deleted by homologous recombination.

In yet another embodiment the genetically engineered thermophilic bacterial cell according to present invention is a gram positive bacterial cell. Preferably the cell belongs to the genus *Bacillus*.

In yet another embodiment the genetically engineered thermophilic bacterial cell according to present invention is a gram positive bacterial cell. Preferably the cell belongs to the genus *Geobacillus*.

In again another embodiment the genetically engineered thermophilic bacterial cell according to present invention is *Geobacillus thermoglucosidans*.

One of the objects of the present invention is to produce a *Geobacillus* strain which is facultative anaerobic and produces (S)-lactic acid by homolactic fermentation.

Chiral purity is an important aspect for production of poly-lactic acid polymers. Therefore, it is essential to produce enantiopure (S)-lactic acid for commercial applications.

Thus, in one aspect, the present invention discloses a method for genetic modification of moderately thermophilic *Geobacillus* species that are facultative anaerobic and homolactic by means of genetic engineering.

In another aspect the invention provides a method to produce enantiomeric pure lactic acid. The method comprises the steps of: culturing a thermophilic bacterial cell according to the present invention using suitable fermentable carbon containing feedstock and isolating the (S)-lactic acid.

In one aspect the invention provides a method to produce enantiomeric pure lactic acid wherein the carbon containing feedstock comprises xylose, glucose or sucrose.

The temperature of the culturing is preferably performed at a temperature of between 50° C. and 70° C., more preferably between 55 and 65° C.

In the context of the invention, inactivation or deletion of a gene may be modification of a gene encoding a desired polypeptide to be produced by the cell and/or a gene encoding a polypeptide involved in production of a primary or secondary metabolite by the cell. In principle this can be done by decreasing the cellular levels of the encoded protein. Decreasing the cellular levels may be effectuated, example gratia, by targeted inactivation of the gene encoding the enzyme of interest. The gene can be removed in its entirety. However, as an alternative also the deletion of part of the gene might result in a reduction of the activity of the encoded protein. Alternatively, or additionally, nucleotide sequences responsible for the regulation or expression of the genes such as promoters enhancers, translational initiator sites and the like can be modified or removed. Another way to influence the activity of the protein of interest might be the modification of transport signals, if needed, or the introduction of anti-sense RNA.

Chromosomal modification is preferred since chromosomal modification will ensure a stable distribution of the functionality of the gene over the progeny cells. Deletion of a desired functionality in the chromosome can be done with non-homologous as well as with homologous recombination. Homologous recombination is preferred, as it opens the opportunity to introduce, to remove or to simultaneously introduce and remove a functionality.

When homologous recombination is intended, the transforming DNA further contains a DNA sequence that is homologous to a genomic target sequence of the specific cell to be engineered. The skilled person will understand that no 100% identity is required to obtain homologous recombination. A percentage identity of 80%, preferably 90%, more preferably 95%, 98% or 99% will also suffice. Generally, the DNA sequence of interest to be inserted in the chromosome by homologous recombination is flanked by homologous sequences with a sufficient length to enable homologous recombination. Such a length may be at least about 200 bp, for instance between about 200 and about 1500 bp, preferably between about 500 and about 1000 bp.

For the purpose of the present invention, the degree of identity between two amino acid sequences refers to the percentage of amino acids that are identical between the two sequences. The degree of identity is determined using the BLAST algorithm, which is described in Altschul, et al., J. Mol. Biol. 215: 403-410 (1990). Software for performing BLAST analyses is publicly available through the National Center for Biotechnology Information (ncbi.nlm.nih.gov/). The default settings for Blastp algorithm parameters are Expect threshold of 10, Word size of 3, Max matches in a query range of 0, Matrix is BLOSUM62, Gap Costs Existence of 11 and Extension of 1, Compositional adjustments at Conditional compositional score matrix adjustment.

For the purpose of the present invention, the degree of identity between two nucleotide sequences refers to the percentage of nucleotides that are identical between the two sequences. The degree of identity is determined using the BLAST algorithm, which is described in Altschul, et al., J. Mol. Biol. 215: 403-410 (1990). Software for performing BLAST analyses is publicly available through the National Center for Biotechnology Information (ncbi.nlm.nih.gov/). The default settings for Blastn algorithm parameters are Expect threshold of 10, Word size of 28, Max matches in a query range of 0, Match/Mismatch Scores of 1, −2, Gap Costs at Linear.

As mentioned hereinbefore, none of sequences identifying the above genes in *Geobacillus thermoglucosidans* need to be 100% identical in order to modify the gene of interest by genetic engineering. Furthermore, in related thermophilic bacterial cells from other species genes might deviate from these sequences. However, making use of the *Geobacillus thermoglucosidans* gene, sequences homologous to these genes and which have the same functionality can easily be identified by those skilled in the art and corresponding primers can be prepared for performing homologous recombination in these strains. Thus, even if deviations from the sequences of the above identified genes exist in a certain strain homologous genes can easily be identified. Its nucleotide sequence can be determined using technologies known in the art and if needed a new set of primers can be defined identical or complementary to the flanking gene sequences.

The cells according to the present invention can be prepared using technologies known in the art. In particular methods to introduce DNA into thermopilic bacteria by electroporation have been described by Van Kranenburg et al., 2007, WO2007/085433 and Cripps et al. 2009, Metab. Eng. 11:398-408.

Transformation of these *Bacillus* species by electroporation can be achieved by a high-voltage discharge through a suspension containing a moderately thermophilic *Bacillus* species that is facultative anaerobic and homolactic and a suitable transforming DNA comprising the desired functionality and/or DNA sequences homologous to genomic sequences of the specific Bacilli.

(S)-Lactic acid can be obtained by fermenting a genetically engineered thermophilic bacterial cell as described herein in the presence of a carbohydrate source (e.g. glucose and/or xylose) by methods known in the art. During fermentation the lactic acid excreted by the micro-organisms is generally neutralized using a base, e.g. basic salts of alkali or alkaline earth metals such as hydroxides, carbonates and/or hydrogen carbonates of sodium, potassium, magnesium, and/or calcium. Magnesium bases, e.g. magnesium hydroxide, magnesium carbonate and/or magnesium hydrogen carbonate, are generally preferred. Accordingly, in several aspects the instant invention particularly relates to a method to produce enantiomeric pure (S)-lactic acid, said method comprising culturing a thermophilic bacterial cell as described herein in the presence of a magnesium base (e.g. selected from at least one of magnesium hydroxide, magnesium carbonate and magnesium hydrogen carbonate) using suitable fermentable carbon containing feedstock and isolating the (S)-lactic acid.

After fermentation, the (S)-lactic acid (or a salt thereof) is separated from the fermentation broth by any of the many conventional techniques known to separate lactic acid and/or lactate from aqueous solutions. Particles of substrate or microorganisms (the biomass) may be removed before separation to enhance separation efficiency. Said separation may be conducted by means of centrifuging, filtration, flocculation, flotation or membrane filtration. This is for instance known from WO 01/38283 wherein a continuous process for the preparation of lactic acid by means of fermentation is described. While the discussion of the fermentation in this specification generally refers to a batch process, parts or all of the entire process may be performed continuously.

After separation of the (S)-lactic acid (or a salt thereof) from the fermentation broth, the product may be subjected to one or more purification steps such as extraction, distillation, crystallization, electrodialysis, filtration, treatment with activated carbon, ion exchange, etcetera. The various residual streams may be recycled, optionally after treatment, to the fermentation vessel or to any previously performed purification step.

EXAMPLES

Materials and Methods
Strains and Plasmids

Strains and plasmids used in this study are listed in Table 1.

*Escherichia coli* was routinely cultured in LB broth (Sambrook & Russell, 2001, Molecular Cloning, a laboratory manual. 3rd edition. Cold Spring Harbor Laboratory Press, New York) at 37° C. under aerobic conditions. When appropriate chloramphenicol and/or ampicillin were used at concentrations of 20 mg/L and 100 mg/L, respectively.

*G. thermoglucosidans* was routinely grown in TGP medium at 52° C., 55° C. or 60° C. under aerobic conditions, unless stated otherwise. TGP medium (Taylor et al., 2008, Plasmid 60:45-52) contained 17 g/L trypton, 3 g/L soy peptone, 5 g/L NaCl, 2.5 g/L $K_2HPO_4$ at pH 7.0, and post-autoclave additions of 4 ml/L glycerol and 4 g/L Na-pyruvate. For TGP plates 10 g/L agar was used. When appropriate, the medium was supplemented with chloramphenicol (8 μg/mL)

TABLE 1

Strains and plasmids used in this study

| Strain or plasmid | Relevant characteristics | Source or reference |
|---|---|---|
| Strains | | |
| *E. coli* TG90 | Plasmid-free strain | Gonzy-Tréboul, G., Karmzyn-Campelli, C., Stragier, P., 1992, J. Mol. Biol. 224: 967-97 |
| *E. coli* DH5α | Plasmid-free strain | ZymoResearch |
| *G. thermoglucosidans* DSM 2542 | *G. thermoglucosidans* type strain | DSMZ, Braunschweig |
| *G. thermoglucosidans* DSM 2542 ΔsigF | Sporulation-deficient *G. thermoglucosidans* | This work |
| *G. thermoglucosidans* ΔsigF, ΔmgsA | Sporulation-deficient, chiral pure, and (S)-lactic acid producing *G. thermoglucosidans* | This work |
| *G. thermoglucosidans* ΔsigF, ΔmgsA, ΔpflBA-ΔadhE | Sporulation-deficient, chiral pure and homolactic, (S)-lactic acid producing *G. thermoglucosidans* | This work |
| Plasmids | | |
| pNW33N | 4.2 kb, $Cm^R$, *E. coli*/*Geobacillus* shuttle vector | *Bacillus* Genetic Stock Centre |
| pRM3 | 6.2 kb, $Cm^R$, pNW33n derivative with the upstream and downstream regions of *G. thermoglucosidans* sigF | This work |
| pJS43 | 6.4 kb, $Cm^R$, pNW33n derivative with upstream and downstream regions of *G. thermoglucosidans* mgsA | This work |
| pRM12 | 6.4 kb, $Cm^R$, pNW33n derivative with upstream and downstream regions of *G. thermoglucosidans* pflBA-adhE locus | This work |

DNA Manipulation Techniques

Standard DNA manipulation techniques were performed as described by Sambrook and Russell (Sambrook & Russell, 2001, Molecular Cloning, a laboratory manual. 3rd edition. Cold Spring Harbor Laboratory Press, New York).

Construction pNW33N derivatives was performed in *E. coli*.

Large-scale *E. coli* plasmid DNA isolation from 100 mL culture was performed using the Jetstar 2.0 Plasmid Maxiprep Kit® (Genomed) following the instructions of the manufacturer. Small-scale *E. coli* plasmid DNA isolation from 1 mL culture was performed using the Nucleospin Plasmid Quick Pure® (Macherey-Nagel) kit following the instructions of the manufacturer.

*E. coli* competent cells were prepared using calcium chloride and transformed by heat shock as described by Sambrook and Russell (Sambrook & Russell, 2001, Molecular Cloning, a laboratory manual. 3rd edition. Cold Spring Harbor Laboratory Press, New York).

PCR reactions for cloning purposes were performed with the high-fidelity Pwo polymerase (Roche) following the instructions of the manufacturer.

For colony-PCR analysis colonies were picked with a tooth pick and a little cell material was transferred to a PCR reaction tube. The cells were disrupted by 1 min incubation at 1000 W in a microwave oven. PCR reaction mixtures of 50 μL or 25 μL with rTaq polymerase (Amersham Biosciences) were prepared as recommended by the manufacturer and added to the reaction tubes with the disrupted cells.

Electroporation of *G. thermoglucosidans*

*G. thermoglucosidans* was transformed by electroporation, based on the protocol described by Cripps et al. (Cripps, et al., 2009, Metab. Eng. 11:398-408). *G. thermoglucosidans* was grown overnight at 55° C. and 1 mL was used to inoculate 50 ml pre-warmed TGP medium in a 250 ml conical flask with baffles. Cells were incubated at 60° C. (180 rpm) until the OD600 was ≅1.0. The flask was cooled on ice for 10 min. and the cells were pelleted by centrifugation (4° C.). Next, the cells were washed four times with ice cold electroporation buffer (0.5 M sorbitol, 0.5 M mannitol, 10% (v/v) glycerol). The volumes of the washing steps were 50 ml, 25 ml, 10 ml, and 10 ml. The final pellet was resuspended in 1.3 ml of ice cold electroporation buffer and 60 µl aliquots of electrocompetent cells were stored at −80° C. or directly used for electroporation.

A 60 µl aliquot of electrocompetent cells (defrosted) was mixed with 1-2 µg plasmid DNA and subsequently transferred to a chilled electroporation cuvet (gap width 0.1 cm). The electroporation conditions using a Bio-Rad gene pulser electroporator were 2.5 kV, 10 µF and 600Ω. After electroporation the cells were transferred to 1 ml of pre-warmed (52° C.) TGP in a 50 ml plastic tube and recovered at 52° C., 180 rpm for two hours. The recovered cell suspension was pelleted and all but 150 µl supernatant was discarded. The pellet was resuspended in the remaining supernatant. Volumes of 1/10 and 9/10 were plated onto TGP plates containing 8 µg/L chloramphenicol. The plates were incubated at 52° C. for 24-48 hours. Colonies which appeared on the plates were transferred to a fresh TGP plate containing 8 µg/L chloramphenicol and incubated at 55° C. overnight. Those that grew were tested for the presence of the plasmid by colony PCR using primers 1 and 2 (Table 2).

Integration

The *Geobacillus*-*E. coli* shuttle vector pNW33n was used as integration vector in *G. thermoglucosidans* as previously described (Cripps et al., 2009 Metab. Eng. 11:398-408). 20 mL TGP containing 8 µg/mL chloramphenicol was inoculated with transformed strains from a glycerol stock. After overnight growth at 55° C., 180 rpm, appropriate dilutions were plated on TGP plates containing 8 µg/mL chloramphenicol. These plates were then incubated at 68° C. for 24 h. Single colonies were streaked to a fresh plate (incubated at 52° C.) and a colony PCR was conducted on these colonies to identify a colony with a single crossover. The appropriate primer combinations were used to identify single crossovers via the upstream or downstream fragment (Table 2; primer combinations 655-170 and 656-571 for integration of pRM3; primer combinations 754-170 and 991-571 for integration of pJS43; primer combinations 744-170 and 808-571 for integration of pRM12, respectively). Next, chromosomal DNA of positive colonies was isolated using the Masterpure Gram Positive DNA Purification Kit (Epicentre Biotechnologies) and to confirm the results of the colony PCR, the PCR described above was repeated on the isolated chromosomal DNA. A single crossover via the upstream flanking region and a single crossover via the downstream flanking region were selected for the second recombination step.

To obtain a double crossover, the primary integrants were sub-cultured several times in TGP without chloramphenicol. Appropriate dilutions ($10^{-4}$, $10^{-5}$, $10^{-6}$) were plated on TGP plates. Isolated colonies were transferred to a TGP plate with and one without 8 µg/mL chloramphenicol. Double crossover mutants are chloramphenicol sensitive. PCR analysis using the appropriate primer combinations (Table 2; primer combinations 655-656 for ΔsigF, 754-991 for ΔmgsA, and 744-808 for ΔpflBA-ΔadhE) was used to discriminate wild-type from deletion mutants and to verify the absence of the plasmid. All modifications were confirmed by sequencing of the PCR products.

TABLE 2

Primers used in this study

| SEQ ID NO | Primer ID | Sequence (5'-3') |
|---|---|---|
| 1 | 1 | TCGCCTTCTTCTGTGTCATC |
| 2 | 2 | CTGGAGGAGAGCAATGAAAC |
| 3 | 651 | GCGCGGGTACCCAGCAAACCGAGCGGAATCAG |
| 4 | 652 | GCGCGGTCGACGGATGGGTAGGCATCCATTC |
| 5 | 653 | GCGCGGTCGACGTCTCCCTTAGTTACATAACGC |
| 6 | 654 | GCGCGAAGCTTGCTTCGCAGTCCAATCGTCGC |
| 7 | 655 | GCTAAGATCGGCCATACGTTAAGC |
| 8 | 656 | GGAGACGAGCTTGGCGTCCTG |
| 9 | 170 | GCCCTCGAGAGGGCTCGCCTTTGGGAAG |
| 10 | 571 | GCTCGTTATAGTCGATCGGTTC |
| 11 | 750 | GCGCGGGATCCGCTTTCCGTTTGCCATTTGCCG |
| 12 | 753 | GCGCGCTGCAGGGCAAGACTGACAGAAGAGCTTGG |
| 13 | 754 | CAGCAGTAACGGCATCCGATTG |
| 14 | 991 | GCGGATATGATTGAATTTGTGACTGCC |
| 15 | 999 | TATGCGACGGGCGCGTGGAGGAATATTGTCCGC |
| 16 | 1000 | ATTCCTCCACGCGCCCGTCGCATACAGTTCATGTTG |
| 17 | 739 | GCGCGGGATCCCCCAAATGGCATTACCGGTGTG |
| 18 | 805 | TGTTATTGCTGGCAGTTTCCCTCCCATGCATCTG |
| 19 | 806 | GGAGGGAAACTGCCAGCAATAACACCAACAGGCTC |
| 20 | 807 | GCGCGCTGCAGCGAAAGCGAACGAAATTGCCAAC |
| 21 | 744 | GCCAAGATGGATATGGGCGTTAGC |
| 22 | 808 | CCGGAGATGGACGGAATTGAAG |

Fermentation

TMM medium was modified from Fong et al. (Fong et al., 2006) and contained per L: 60 g/L glucose; 30 g/L xylose; 8.37 g MOPS, 0.23 g $K_2HPO_4$; 0.51 g $NH_4Cl$; 0.50 g NaCl; 1.47 g $Na_2SO_4$; 0.08 g $NaHCO_3$; 0.25 g KCl; 1.87 g $MgCl_2.6H_2O$; 0.41 g $CaCl_2.2H_2O$; 16.0 mg $MnCl_2.4H_2O$; 1.0 mg $ZnSO_4.7H_2O$; 2.0 mg $H_3BO_3$; 0.1 mg $CuSO_4.5H_2O$; 0.1 mg $Na_2MoO_4.2H_2O$; 1.0 mg $CoCl_2.6H_2O$; 7.0 mg $FeSO_4.7H_2O$; 0.1 mg thiamine; 0.1 mg riboflavin; 0.5 mg nicotinic acid; 0.1 mg panthothenic acid; 0.5 mg pyridoxamine, HCl; 0.5 mg pyridoxal, HCl; 0.1 mg D-biotin; 0.1 mg folic acid; 0.1 mg p-aminobenzoic acid; 0.1 mg cobalamin. pH was adjusted to pH 7.2. Glucose, xylose, metals and vitamins were filter sterilized. Medium was autoclaved. TMM1, TMM2.5, and TMM5 were supplemented with 1 g/L, 2.5 g/L, and 5 g/L yeast extract (Oxoid), respectively.

STMM medium, differed from TMM medium in concentrations of $K_2HPO_4$ (1.00 g/L), $NH_4Cl$ (2.50 g/L), NaCl (5.00 g/L), and $CaCl_2.2H_2O$ (50 mg/L) and was supplemented with D,L-methionine (68.5 mg/L) and betaine (0.14 g/L).

A 100 mL preculture in TMM5 or STMM5 was used to inoculate (10% v/v) 400 mL TMM1 or TMM2.5, or STMM2.5 or STMM5, respectively, in a 0.75 L Multifors fermentor (Infors) equipped with a condenser (cooled with running tap water of approximately 15° C.). The pH was controlled at pH 7.2 by addition of sterile 2.5 M KOH, sterile 75 g/L Mg(OH)$_2$, or sterile 75 g/L Ca(OH)$_2$. Temperature was 60° C. Stirrer speed was 300 rpm.

Samples were withdrawn from the fermentation for measurement of (R)- and (S)-lactic acid, and possible by-products. Samples were centrifuged and remaining debris was removed by filtration using a Millex GP 0.22 µm filter® (Millipore). Filtrate was stored at −21° C. until further analysis.

Sugars were measured by HPLC using an Thermo CarboPac SA-10 column (Dionex). Organic acids (lactic acid, acetic acid, formic acid, succinic acid, fumaric acid, pyruvic acid) and ethanol were measured using a derivatisation and gas-liquid chromatography (GLC). (R)- and (S)-lactates were methylated to methyl-lactate and measured by headspace analysis on a chiral column.

Example 1

Enantiopure Lactic Acid Production with *G. thermoglucosidans*

Integration plasmid pRM3 was constructed to delete the sigF gene in *G. thermoglucosidans*. The upstream and downstream flanking regions of the sigF gene were generated by PCR using genomic DNA of DSM 2542 as template and primer combinations 653 and 654 (Table 2) to obtain the upstream fragment, and the primers 651 and 652 (Table 2) to obtain the downstream fragment. First, the downstream fragment was cloned as KpnI-SalI fragment into pNW33n, digested with the same enzymes. Next, the upstream fragment was cloned as SalI-HindIII fragment into this construct, digested with the same enzymes resulting in plasmid pRM3. Construction of pRM3 was done in *E. coli* TG90. The integrity of the pRM3 sequence was confirmed by DNA sequencing.

Plasmid pRM3 was electroporated to *G. thermoglucosidans* DSM 2542. A single transformant colony was selected and used to obtain single crossover mutants as described in Materials and Methods. Two colonies were selected for further work, one with a single crossover via the upstream flanking region and one with a single crossover via the downstream flanking region.

A double crossover mutant was obtained following the procedure described in Materials and Methods. Sixty colonies, obtained after subculturing of the single crossover integrants in TGP without chloramphenicol, were transferred to TGP plates with and without chloramphenicol. Fifteen colonies were sensitive to chloramphenicol. Twelve colonies had the desired modification and three had reverted to wild-type. One colony was selected and designated *G. thermoglucosidans* DSM 2542 ΔsigF. The deletion was confirmed by sequencing.

*G. thermoglucosidans* DSM 2542 ΔsigF was evaluated in pH-controlled (KOH) fermentation using TMM1 and TMM2.5. Fermentations were analysed. The results are summarized in Table 3. *G. thermoglucosidans* DSM 2542 ΔsigF consumed xylose and glucose simultaneously. Chiral purity of the (S)-lactic acid produced was well below specs for chiral pure lactic acid.

Plasmid pJS43 was constructed to delete 267 bp of the mgsA gene (423 bp) in *G. thermoglucosidans*. The upstream and downstream flanking regions of the mgsA gene were generated by PCR using genomic DNA of DSM 2542 as template and primer combinations 750 and 999 to obtain the mgsA downstream fragment, and the primers 1000 and 753 to acquire the upstream mgsA fragment. The resulting two PCR-products were subsequently used as template in an overlap-PCR using primer combination 750 and 753 to fuse them together. The product was cloned as BamHI-PstI fragment into plasmid pNW33n digested with BamHI and PstI, resulting in plasmid pJS43. Construction of pJS43 was done in *E. coli* TG90. Integrity of the pJS43 nucleotide sequence was confirmed by sequencing.

Plasmid pJS43 was electroporated to *G. thermoglucosidans* DSM 2542 ΔsigF. A single transformant colony was selected and used to obtain single crossover mutants as described in Materials and Methods. One single-crossover integrant was selected for further work.

A double crossover mutant was obtained following the procedure described in Materials and Methods. Sixty colonies. obtained after subculturing of the single crossover integrant in TGP without chloramphenicol, were transferred to TGP plates with and without chloramphenicol. All colonies appeared chloramphenicol sensitive. Twenty-five colonies were analysed. Four colonies had the desired modification and twenty-one had reverted to wild-type. One colony was selected and designated *G. thermoglucosidans* DSM 2542 ΔsigF, ΔmgsA. The deletion was confirmed by sequencing.

*G. thermoglucosidans* DSM 2542 ΔsigF, ΔmgsA was evaluated in pH-controlled fermentation (Mg(OH)$_2$) using STMM2.5. The fermentation was analysed. The results are summarized in Table 4. *G. thermoglucosidans* DSM 2542 ΔsigF, ΔmgsA consumed xylose and glucose simultaneously. Chiral purity of the (S)-lactic acid produced was 99.6%, which is considered chiral pure. These data clearly show that despite the apparent incompleteness of the methylglyoxal pathway in *G. thermoglucosidans*, disruption of mgsA results in the ability to produce chiral pure (S)-lactic acid.

TABLE 3

Fermentations with *G. thermoglucosidans* DSM 2542 ΔsigF on a glucose/xylose mixture.

| Time (h) | Glucose (g/L) | | Xylose (g/L) | | Total lactic acid (g/kg) | | Chiral purity (S)-lactic acid (%) | |
|---|---|---|---|---|---|---|---|---|
| | TMM1 | TMM2.5 | TMM1 | TMM2.5 | TMM1 | TMM2.5 | TMM1 | TMM2.5 |
| 24 | 41.1 | 18.5 | 16.6 | 11.4 | 1.6 | 2.9 | 90.4 | 89.5 |
| 48 | 38.6 | 15.2 | 12.0 | 7.0 | 1.8 | 3.3 | 89.5 | 89.4 |

TABLE 4

Fermentation with *G. thermoglucosidans*
DSM 2542 ΔsigF, ΔmgsA on STMM2.5

| Time (h) | Glucose (g/kg) | Xylose (g/kg) | Total lactic acid (g/kg) | Chiral purity (S)-lactic acid (%) | Acetic acid (g/kg) | Formic acid (g/kg) | Ethanol (g/kg) |
|---|---|---|---|---|---|---|---|
| 24 | 1.16 | 6.04 | 49 | 99.6 | 0.7 | 2.9 | 2.6 |

Example 2

Enantiopure Homolactic Acid Production with *G. thermoglucosidans*

*G. thermoglucosidans* DSM 2542 ΔsigF, ΔmgsA still produced significant amounts of formic acid and ethanol, while acetic acid was a minor by-product (Table 4). Although mutations of pflA and/or pflB and adhE are known to impact formic acid and ethanol production in many bacteria, the side effects of disrupting those genes are unpredictable.

Plasmid pRM12 was constructed to delete the genes pflB, pflA and adhE (partially) in *G. thermoglucosidans*. The upstream flanking region of pflBA and the upstream flanking region of the convergently oriented adhE were generated by PCR using genomic DNA of DSM 2542 as template and primer combinations 739 and 805 to obtain the upstream pflBA fragment and the primers 806 and 807 to acquire the upstream adhE fragment. The resulting two PCR-products were subsequently used as template in an overlap-PCR using primer combination 739 and 807 to fuse them together. The product was cloned as BamHI-PstI fragment into plasmid pNW33n digested with BamHI and PstI, resulting in plasmid pRM12. Construction of pRM12 was done in *E. coli* DH5a. Integrity of the pRM12 nucleotide sequence was confirmed by sequencing.

Plasmid pRM12 was electroporated to *G. thermoglucosidans* DSM 2542 ΔsigF, ΔmgsA. A single transformant colony was selected and used to obtain single crossover mutants as described in Materials and Methods. Two colonies were selected for further work, one with a single crossover via the upstream pflBA flanking region and one with a single crossover via the upstream adhE flanking region.

A double crossover mutant was obtained following the procedure described in Materials and Methods. Hundred-and-twenty colonies, obtained after subculturing of the single crossover integrants in TGP without chloramphenicol, were transferred to TGP plates with and without chloramphenicol. Two colonies were sensitive to chloramphenicol. One had the desired modification and the other had reverted to wild-type. The one colony was designated *G. thermoglucosidans* DSM 2542 ΔsigF, ΔmgsA, ΔpflBA-ΔadhE. The deletion was confirmed by sequencing.

TABLE 5

Fermentation with *G. thermoglucosidans* DSM 2542 ΔsigF, ΔmgsA, ΔpflBA-ΔadhE on TMM5

| Time (h) | Glucose (g/kg) | Xylose (g/kg) | Total lactic acid (g/kg) | Chiral purity (S)-lactic acid (%) | Acetic acid (g/kg) | Formic acid (g/kg) | Ethanol[1] (g/kg) |
|---|---|---|---|---|---|---|---|
| 0[1] | 49.4 | 22.6 | 4.5 | n.d.[2] | <0.1 | 0.8 | 0.3 |
| 24 | 30.2 | 16.0 | 24.0 | 99.8 | 0.1 | 0.8 | 0.2 |
| 48 | 22.7 | 11.7 | 30 | 99.7 | 0.2 | 1.0 | 0.2 |

[1]Sampling after inoculation.
[2]n.d. = not determined: lactic acid concentration too low to determine chiral purity (—

*G. thermoglucosidans* DSM 2542 ΔsigF, ΔmgsA, ΔpflBA-ΔadhE was evaluated in pH-controlled (Ca(OH)$_2$) fermentations using STMM medium containing 5.0 g/L yeast extract, 60 g/L glucose and 30 g/L xylose. The fermentation was analysed at three time points. The results are summarized in Table 5. *G. thermoglucosidans* DSM 2542 ΔsigF, ΔmgsA, ΔpflBA-ΔadhE consumed xylose and glucose simultaneously. Chiral purity of the (S)-lactic acid produced by *G. thermoglucosidans* DSM 2542 ΔsigF, ΔmgsA, ΔpflBA-ΔadhE was 99.7% or higher. Acetic acid and formic acid production was 6.7 mg per gram of lactic acid. Ethanol production could not be detected. These data clearly demonstrate that disruption of the pyruvate-formate lyase and alcohol dehydrogenase complex genes significantly reduce the production of ethanol, formic acid, and acetic acid resulting in a homolactic and chiral pure (S)-lactic acid fermentation.

The invention claimed is:

1. A genetically engineered thermophilic bacterial cell that is facultative anaerobic, gram positive, (S)-lactic acid producing, and belongs to the genus *Geobacillus* comprising:
   inactivation or deletion of the endogenous methylglyoxal synthase gene mgsA, wherein the bacterial cell is homolactic and produces (S)-lactic acid with an enantiomeric purity of at least 98%.

2. The cell according to claim 1 wherein in addition the endogenous pyruvate-formate lyase A and/or B gene is inactivated or deleted.

3. The cell according to claim 1 which is a sporulation deficient derivative due to inactivation or deletion of an endogenous sporulation gene.

4. The cell according to claim 3 wherein the sporulation gene is sigF.

5. The cell according to claim 2 wherein the endogenous pyruvate-formate lyase A and/or B gene is inactivated by inactivation or deletion of the pyruvate-formate lyase/alcohol dehydrogenase locus pflBA-adhE.

6. The cell according to claim 1 which produces (S)-lactic acid with an enantiomeric purity of at least 99%.

7. The cell according to claim 1 wherein in addition the endogenous phosphotransacetylase gene (pta) is inactivated or deleted.

8. The bacterial cell according to claim 1 wherein the genes are inactivated or deleted by homologous recombination.

9. The cell according to claim 1 wherein the *Geobacillus* species is *Geobacillus thermoglucosidans*.

10. A method to produce enantiomeric pure (S)-lactic acid, said method comprising culturing a thermophilic bacterial cell according to claim 1 using suitable fermentable carbon containing feedstock and isolating the (S)-lactic acid.

11. The method according to claim 10 wherein the carbon containing feedstock comprises xylose, glucose or sucrose.

12. The method according to claim 10 wherein the culturing is performed at a temperature of between 50° C. and 70° C.

13. The method according to claim 10 wherein no more than 15% (w/w) of by-products are formed, based on the total weight of byproducts over the total weight of lactic acid produced.

14. The method according to claim 10 wherein the formed amount of at least one of formic acid, ethanol and acetic acid is no more than 10% (w/w) based on the total weight of formic acid, ethanol or acetic acid over the total weight of lactic acid produced.

* * * * *